(12) United States Patent
Capodieci et al.

(10) Patent No.: US 8,062,897 B2
(45) Date of Patent: *Nov. 22, 2011

(54) DIAGNOSTIC HISTOPATHOLOGY USING MULTIPLEX GENE EXPRESSION FISH

(75) Inventors: Paola Capodieci, New York, NY (US); Michael J. Donovan, Boston, MA (US)

(73) Assignee: Aureon Laboratories, Inc., Yonkers, NY (US)

( * ) Notice: Subject to any disclaimer, the term of this patent is extended or adjusted under 35 U.S.C. 154(b) by 234 days.

This patent is subject to a terminal disclaimer.

(21) Appl. No.: 11/404,272

(22) Filed: Apr. 14, 2006

(65) Prior Publication Data

US 2006/0199213 A1    Sep. 7, 2006

Related U.S. Application Data

(63) Continuation-in-part of application No. 11/283,062, filed on Nov. 17, 2005, now Pat. No. 7,326,575, which is a continuation of application No. 10/624,233, filed on Jul. 21, 2003, now Pat. No. 6,995,020.

(60) Provisional application No. 60/671,549, filed on Apr. 15, 2005, provisional application No. 60/707,612, filed on Aug. 12, 2005.

(51) Int. Cl.
*G01N 33/00* (2006.01)
*G01N 33/53* (2006.01)
*C07H 21/04* (2006.01)

(52) U.S. Cl. ......... 436/94; 436/800; 536/23.1; 536/24.3

(58) Field of Classification Search .................. None
See application file for complete search history.

(56) References Cited

U.S. PATENT DOCUMENTS

| | | | | |
|---|---|---|---|---|
| 5,474,796 A * | 12/1995 | Brennan | ............. | 427/2.13 |
| 5,672,696 A | 9/1997 | Wang et al. | ............. | 536/25.42 |
| 5,750,340 A | 5/1998 | Kim et al. | ............. | 435/6 |
| 5,856,089 A | 1/1999 | Wang et al. | ............. | 435/6 |
| 6,165,723 A | 12/2000 | Shah et al. | ............. | 435/6 |
| 6,248,535 B1 | 6/2001 | Danenberg et al. | ............. | 435/6 |
| 6,534,266 B1 | 3/2003 | Singer | ............. | 435/6 |
| 6,544,798 B1 | 4/2003 | Christensen et al. | ............. | 436/177 |
| 6,573,043 B1 | 6/2003 | Cohen et al. | ............. | 435/6 |
| 6,580,056 B1 | 6/2003 | Tacha | ............. | 219/440 |
| 6,995,020 B2 * | 2/2006 | Capodieci et al. | ............. | 436/94 |
| 7,326,575 B2 * | 2/2008 | Capodieci et al. | ............. | 436/94 |
| 2002/0192702 A1 | 12/2002 | Kononen et al. | ............. | 435/6 |
| 2003/0040035 A1 | 2/2003 | Slamon et al. | ............. | 435/40.5 |
| 2003/0170852 A1 * | 9/2003 | Allikmets et al. | ............. | 435/194 |
| 2004/0038270 A1 | 2/2004 | Muhlhahn et al. | ............. | 435/6 |
| 2004/0265928 A1 * | 12/2004 | Kennedy | ............. | 435/7.23 |
| 2006/0141502 A1 | 6/2006 | Capodieci et al. | ............. | 435/6 |

FOREIGN PATENT DOCUMENTS

WO    WO 2005/010203    2/2005

OTHER PUBLICATIONS

Anastasi et al.; Blood 77:2456-2462 (1991).
Anastasi et al.; Blood 79:1796-1801 (1992).
Anastasi et al.; Blood 81:1580-1585 (1993).
Baschong, et al.; The Journal of Histochemistry & Cytochemistry, 49:1565-1571 (2001).
Bubendorf L., et al.; J Pathol 195, 72 (2001).
Bussemakers MJ et al.; Cancer Res. 59, 5975-5979 (1999).
Capodieci P. et al.; Nature Methods, 2:663-665 (2005).
Capodieci P., et al.; Diagn Mol Pathol 7, 69 (1998).
Capodieci P., et al.; J Natl Cancer Inst. 96, (2004).
Chin S., et al.; Molecular Biology, 56:275-279 (2003).
Cronin M et al.; Amer J Pathol 164, 35 (2004).
Debes et al.; Cancer Res 63, 7638 (2002).
Debes et al.; Cancer Res 65, 708 (2005).
Enders G. Acta Neurochir Suppl. 89,9-13 (2004).
Engel, et al.; Journal of Clinical Pathology, 50:37-39 (1997).
Femino, A. M., et al.; Science 280, 585 (1998).
Glinsky G., et al.; J Clin Invest. 113, 913-923 (2004).
Heighway J et al.; Oncogene 21,7749-7763 (2002).
Hoffmann K, et al.; UR Mol Biotechnol. 29,31-38 (2005).
Kosman D., et al.; Science, 305, 846 (2004).
Levsky, J. M., et al.; Science 297, 836 (2002).
Lewis F., et al.; J Pathol. 195, 66 (2001).
Lockhart, D. J. and E. A. Winzeler Nature 405(6788): 827-36 (2000).
Lu et al.; Nature, 435,834-838 (2005).
Nguyen et al.; J. Biol. Chem., 277(44):41960-9 (2002).
Paik et al.; NEJM 351, 2817 (2004).
Paris et al.; Science, Jul. 13;293 (5528):293-7 (2001).
Petersen, B, et al.; Applied Immunohistochemistry & Molecular Morphology, AIMM/Official Publication of the Society for Applied Immunohistochemistry, 12:259-265 (2004).
Shou J., et al.; Cancer Res. 61, 7219-7297 (2001).
van de Vijver MJ et al.; NEJM 347,1999-2009 (2002).
van Lom et al.; Blood 82:884-888 (1992).
Wilson AJ, et al.; Cancer Res. 62,6006-6010 (2002).
Wolman et al.; Diagnostic Molecular Pathology 1(3): 192-199 (1992).
Zitzelberger, Journal of Pathology 172:325-335 (1994).
International Search Report corresponding to PCT/US06/014664 mailed Oct. 20, 2006.
Zheng, Ghohong, et al. "Localization of pre-mRNA splicing in mammalian nuclei" *Nature* vol. 372, pp. 809-812, Dec. 1994.

* cited by examiner

*Primary Examiner* — Bradley L Sisson
(74) *Attorney, Agent, or Firm* — Mintz Levin Cohn Ferris Glovsky and Popeo, P.C.; Richard G. Gervase, Esq.; Cynthia A. Kozakiewicz

(57) ABSTRACT

The present invention relates to a method for detecting one or more nascent RNAs in a tissue sample using FISH. In the method, a plurality of probes (8 to 82) may be used to detect a single species of nascent RNA. Further, a plurality of nascent RNA species may be detected simultaneously using between 8 and 82 probes for each nascent RNA. The invention comprises, in addition, methods of preparing a sample for nascent RNA detection by reducing autofluorescence of the tissue sample. These techniques may be synergistically combined to achieve significantly improved results.

22 Claims, 18 Drawing Sheets
(16 of 18 Drawing Sheet(s) Filed in Color)

1 AR
2 PSMA
3 JAG-1
4 AMACR
5 EPB49

10 μm

10 μm

1 AR
2 PSMA
3 JAG-1
4 AMACR
5 EPB49

FIG. 2F

|  | AMACR | PSMA | AR | EPB4.9 | JAG-1 |
|---|---|---|---|---|---|
| PCa vs PIN | 0.007435* | 0.000989* | 0.019115* | 0.225716 | 0.145484 |
| PCa vs PCaMet | 0.002872* | 0.000232* | 0.000032* | 0.000091* | - |
| PCa vs Benign | 0.000068* | 0.000181* | 0.000005* | 0.383469 | 0.004207* |
| PCa vs PCaMet | 0.225270 | 0.145176 | 0.062813 | 0.005669* | - |
| PIN vs Benign | 0.002112* | 0.121016 | 0.020870* | 0.174033 | 0.175670 |
| PCaMet vs Benign | 0.044623* | 0.414225 | 0.162582 | 0.001140* | - |

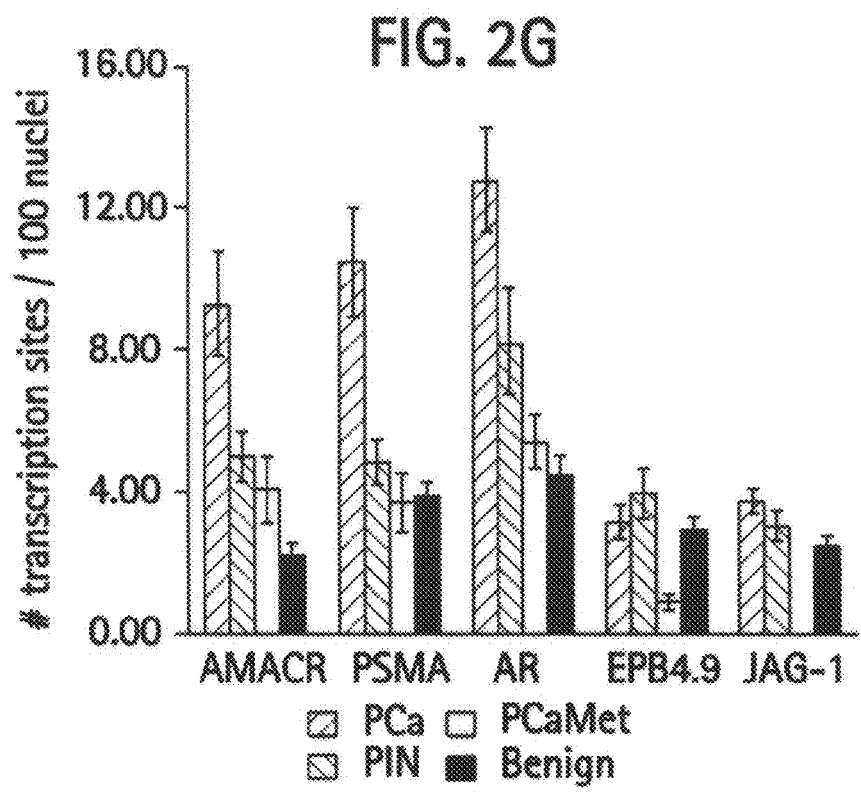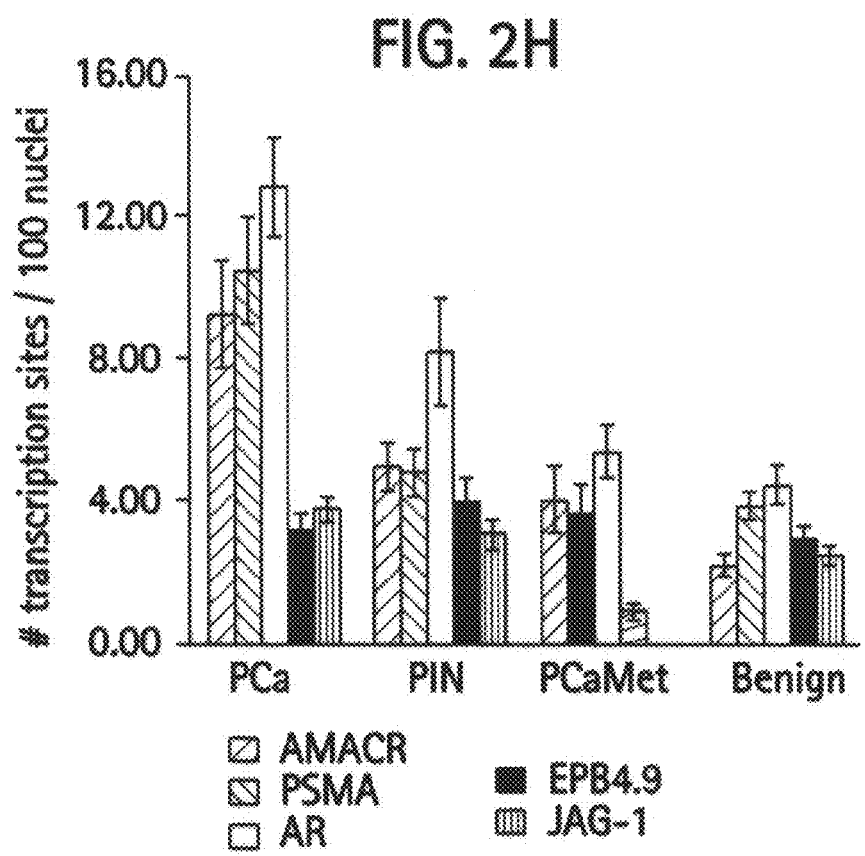

5 μm

1 AR
2 PSMA
3 JAG-1
4 AMACR
5 EPB49

10 μm

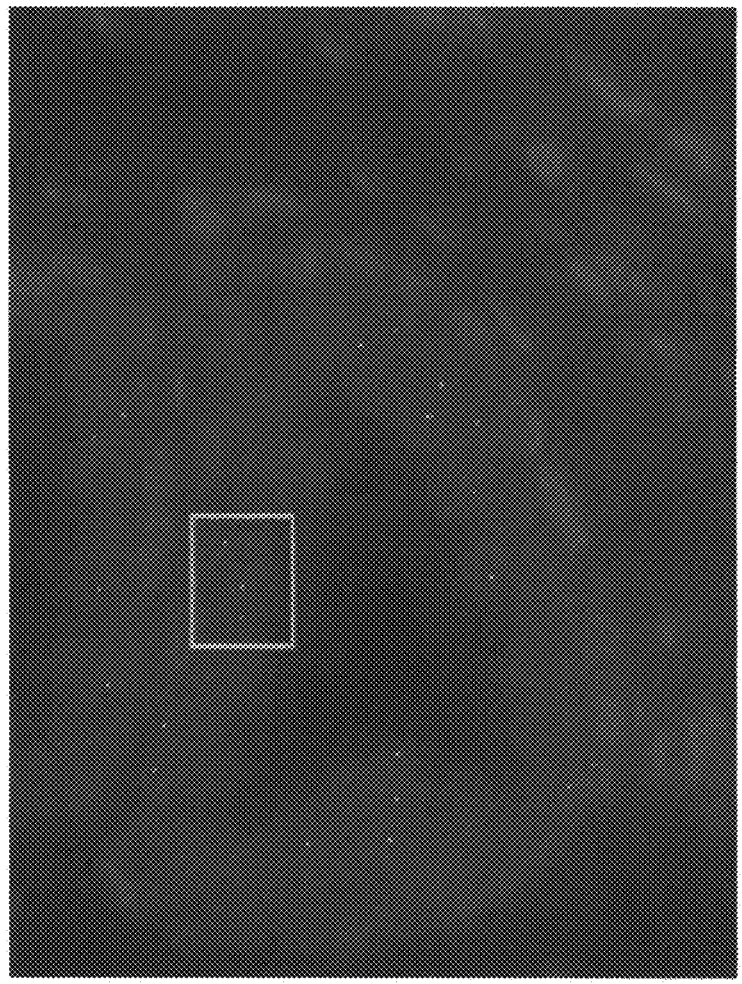
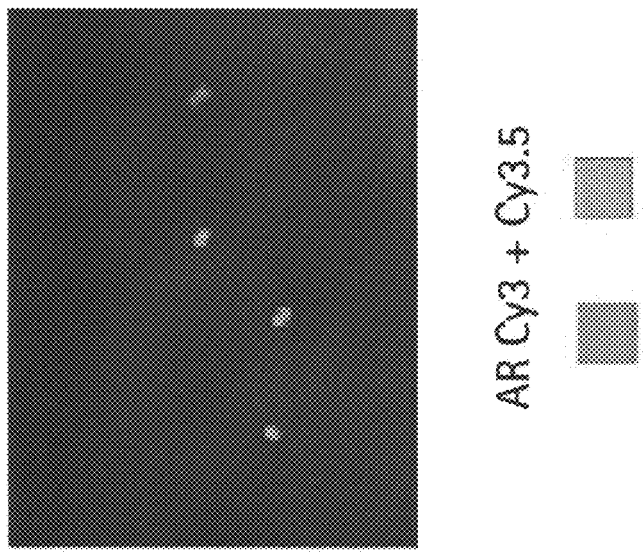
AR Cy3 + Cy3.5
FIG. 7

SEQUENCE LISTING

<160> NUMBER OF SEQ ID NOS: 20

<210> SEQ ID NO 1
<211> LENGTH: 50
<212> TYPE: DNA
<213> ORGANISM: Artificial
<220> FEATURE:

-continued

<223> OTHER INFORMATION: Synthetic Oligonucleotide

<400> SEQUENCE: 1
gtgcttagag ggagatcatg aacaccaaga caaaaggcct ggatgcaacc                50

<210> SEQ ID NO 2
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 2
ggcttgtaac ttaactcagt ccaaggagac acaaaacgac ttgctggggg                50

<210> SEQ ID NO 3
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 3
gatgaagaaa cctgctccac cttcctcttg cgattgttga acggcagttg                50

<210> SEQ ID NO 4
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 4
ttccttccac catatttgca tcaatgacct gacccttgcc agtgcgtgtg                50

<210> SEQ ID NO 5
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 5
cttccacatg tgagagctcc atagtgacac ccagaagctt catctccaca                50

<210> SEQ ID NO 6
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 6
tctccttcct cctgtagttt cagattacca agtttcttca gcttccgggc                50

<210> SEQ ID NO 7
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 7
catagccttc aatgtgtgac actgtcagct tctgggttgt ctcctcagtg                50

<210> SEQ ID NO 8

```
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 8
tgtgcatgcg gtactcattg aaaaccagat cagggggcgaa gtagagcatc            50

<210> SEQ ID NO 9
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 9
ccacctcccg gctttctttc cttctctcgc gctcccctcc ttttattatt            50

<210> SEQ ID NO 10
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 10
acacggctga tgagtcccac agtaattgag atctttgtca cagagctggc            50

<210> SEQ ID NO 11
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 11
agcgataacc attaaccaaa tcccgacagg aggcgtcatt ctgacactgg            50

<210> SEQ ID NO 12
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 12
agtagtagtc atcacaggtc acgcggatct gatactcaaa gtgggcaacg            50

<210> SEQ ID NO 13
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 13
ggtaaagtct ctctcaatct cactaatgcc tcgcttatca gccctgcagg            50

<210> SEQ ID NO 14
<211> LENGTH: 49
<212> TYPE: DNA
<213> ORGANISM: Artificial
<220> FEATURE:
<223> OTHER INFORMATION: Synthetic Oligonucleotide

<400> SEQUENCE: 14
```

-continued aggattttaa aaccacccga agaggaagcc gaggagaaag aagccaccc    49

<210> SEQ ID NO 15
<211> LENGTH: 49
<212> TYPE: DNA
<213> ORGANISM: Artificial
<220> FEATURE:
<223> OTHER INFORMATION: Synthetic Oligonucleotide

<400> SEQUENCE: 15
gggtaggaca acaggacatc ataatgtgct agctcaacag aatcaggcc    49

<210> SEQ ID NO 16
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 16
aggtccaaca ttgtagggca ctttgagact tcctctccag ctgctatctg    50

<210> SEQ ID NO 17
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 17
gccggctggt gcagacagta agtgaattat gaaacgaggc aagtcatcca    50

<210> SEQ ID NO 18
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 18
gcagagagcg ggttttcctt cggatcggca atgactttc catctcttct    50

<210> SEQ ID NO 19
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 19
ggggccccaa taaattacat tcttgagaga gcatagtgtg tgaggggtg    50

<210> SEQ ID NO 20
<211> LENGTH: 50
<212> TYPE: DNA
<213> ORGANISM: Artificial
<220> FEATURE:
<223> OTHER INFORMATION: Synthetic Oligonucleotide

<400> SEQUENCE: 20
tatagatggg aggcttcttg tagatgttgg aatctgggcg ggaggtctca    50

DIAGNOSTIC HISTOPATHOLOGY USING MULTIPLEX GENE EXPRESSION FISH

RELATED APPLICATIONS

This application is a continuation-in-part of U.S. Pat. No. 7,326,575, Ser. No. 11/283,062 filed Nov. 17, 2005 and issued Feb. 5, 2008, which is a continuation of U.S. Pat. No. 6,995,020, Ser. No. 10/624,233, filed Jul. 21, 2003 and issued Feb. 7, 2006. This application also claims the benefit of priority from U.S. 60/671,549, filed Apr. 15, 2005, and U.S. 60/707,612, filed Aug. 12, 2005. All patents, patent applications and references cited in this specification are hereby incorporated by reference.

BACKGROUND OF THE INVENTION

Advancements in the understanding of gene expression and epidemiology combined with developments in technology have allowed for the correlation of genetic expression with, for example, disease states. An accurate correlation may enable risk assessment for an individual based on the expression profile of their individual cells. Further, drug screening and other research based protocols may quickly generate data in cell lines or tissue samples that can be extended to develop treatments for human disease.

Most of the methodologies available for evaluation of cell lines or tissue have well-known drawbacks. For example, most gene expression analyses extract RNA from solubilized tissue, which destroys cellular architecture such that expression profiles can not be associated with specific cell types. Analysis of small samples excludes the detection of a large number of potentially interesting low abundance gene products. Lack of standardization and reproducibility and amplification bias limit the interpretation of expression data resulting from methods such as RNA amplification and quantitative PCR (Bubendorf L., et al. J. Pathol. 195, 72 (2001); Capodieci P., et al. Diagn. Mol. Pathol. 7, 69 (1998); Femino, A. M., et al. Science 280, 585 (1998)). In addition, methods that require disaggregation of the sample, such as Southern, Northern, or Western blot analysis, are rendered less accurate by dilution of the malignant cells by the normal or otherwise non-malignant cells that are present in the same sample. Furthermore, the resulting loss of tissue architecture precludes the ability to correlate, for example, malignant cells with the presence of genetic abnormalities in a context that allows morphological specificity. This issue is particularly problematic in tissue types known to be heterogeneous, such as in human breast carcinoma, where a significant percentage of the cells present in any area may be non-malignant.

Another drawback is that many of the art recognized techniques require the tissue being analyzed to be fresh. Typically, however, it is not always possible in the clinical setting to work on cell lines or tissue as soon as they are available. Accordingly, cell lines or tissue are often preserved in paraffin. Processes for treating a paraffin-embedded tissue sample for gene analysis have been described, for example, U.S. Pat. Nos. 5,672,696 and 6,248,535. Typically treatments comprise treating tissue cells freed of paraffin with a solution containing a surfactant, a protease, etc. at room temperature to upwards of 60° C. for 4 to 48 hours to disrupt the tissue cells, removing impurities (i.e., substances other than nucleic acid) by a two-phase separation method (i.e., a method comprising separation into an aqueous phase containing the nucleic acid and an organic solvent phase containing denatured protein and the like by addition of one or more organic solvents such as phenol, chloroform, etc.), and then adding an alcohol to the residue to precipitate the nucleic acid in the aqueous phase (Jikken Igaku, Vol. 8, No. 9, pp. 84-88, 1990, Yodosha Co., Ltd.). While this technique allows for the analysis of gene expression, the purification disrupts cellular architecture and does not allow the application of in situ hybridization techniques.

As described in U.S. Pat. Nos. 5,750,340 or 6,165,723, in situ hybridization (ISH) is a powerful and versatile tool for the detection and localization of nucleic acids (DNA and RNA) within cell or tissue preparations. By the use of labeled DNA or RNA probes, the technique provides a high degree of spatial information in locating specific DNA or RNA target within individual cells or chromosomes. ISH is widely used for research and potentially for diagnosis in the areas of prenatal genetic disorders, and molecular cytogenetics. In the general area of molecular biology, ISH is used to detect gene expression, to map genes, to identify sites of gene expression, to localize target genes, and to identify and localize various viral and microbial infections. Currently, the application of the ISH technology research is being expanded into tumor diagnosis, preimplantation genetic diagnosis for in vitro fertilization, evaluation of bone marrow transplantation, and analysis of chromosome aneuploidy in interphase and metaphase nuclei.

In ISH, labeled nucleic acids (DNA or RNA) are hybridized to chromosomes, DNA or mRNAs in cells which are immobilized on microscope glass slides (In Situ Hybridization: Medical Applications (eds. G. R. Coulton and J. de Belleroche), Kluwer Academic Publishers, Boston (1992); In Situ Hybridization: In Neurobiology; Advances in Methodology (eds. J. H. Eberwine, K. L. Valentino, and J. D. Barchas), Oxford University Press Inc., England (1994); In Situ Hybridization: A Practical Approach (ed. D. G. Wilkinson), Oxford University Press Inc., England (1992)). Numerous non-isotopic systems have been developed to visualize labeled DNA probes including, for example, a) fluorescence-based direct detection methods, b) the use of digoxigenin- and biotin-labeled DNA probes coupled with fluorescence detection methods, and c) the use of digoxigenin- and biotin-labeled DNA probes coupled with antibody-enzyme detection methods. When fluorescence-labeled nucleic acid (DNA or RNA) probes are hybridized to cellular DNA or RNA targets, the hybridized probes can be viewed directly using a fluorescence microscope. By using multiple nucleic acid probes with different fluorescence colors, simultaneous multicolored analysis (i.e., for multiple genes or RNAs) can be performed in a single step on a single target cell (Levsky et al. Science 2001). Fluorochrome-directly labeled nucleic acid probes eliminate the need for multi-layer detection procedures (e.g., antibody-based system), which allows for fast processing and also reduces non-specific background signals. Therefore, fluorescence in situ hybridization "FISH" has become an increasingly popular and valuable tool in both basic and clinical sciences.

Unfortunately, although FISH is an extremely useful technique, detection of mRNA, especially pre-mRNA (hnRNA, nascent RNA etc) in paraffin-embedded or otherwise fixed-treated cell lines or tissue (i.e., "fixed-treated tissue" defined as tissue that is not fresh frozen) is currently difficult, if not impossible. FISH is a highly sensitive assay that allows the detection of nucleic acid within undisturbed cellular and tissue architecture and the use of synthetic oligomer probes in FISH has improved the sensitivity of the process; however, to date FISH has only been successfully conducted in cells grown through cell-line culture. mRNA detection through FISH has not been successfully conducted in tissue until just recently (Nguyen et al., J Biol Chem, November 1; 277 (44): 41960-9 (2002)); Paris et al., Science, July 13; 293 (5528): 293-7 (2001)).

Detection is difficult for a number of reasons, including interference caused by the creation of chemical bonds during fixation processes as well as native autofluorescence in the cell lines or tissue. The ability to easily apply FISH to such cell lines or tissue would be of great interest because of the large amount of clinically relevant cell lines and tissue that have been (and continue to be) preserved in this fashion.

U.S. Pat. No. 5,856,089 describes in situ hybridization methods using nucleic acid probes for single copy sequences for detecting chromosomal structural abnormalities in fixed tissue obtained from a patient suspected of having a chromosomal structural abnormality. The methods include the use of bisulfite ion on the fixed cells.

U.S. Pat. No. 5,672,696 describes preparation of a sample for a gene analysis or high-purity nucleic acid suitable for gene amplification from a paraffin-embedded tissue sample comprising heating an aqueous suspension containing a surfactant having a protein-denaturation action and a deparaffinized tissue sample obtained from a paraffin-embedded tissue sample at 60° C. or higher. However, it is not an object of this patent to preserve the cellular architecture.

FISH has historically been combined with classical staining methodologies in an attempt to correlate genetic abnormalities with cellular morphology (see e.g., Anastasi et al., Blood 77:2456-2462 (1991); Anastasi et al., Blood 79:1796-1801 (1992); Anastasi et al., Blood 81:1580-1585 (1993); van Lom et al., Blood 82:884-888 (1992); Wolman et al., Diagnostic Molecular Pathology 1 (3): 192-199 (1992); Zitzelberger, Journal of Pathology 172:325-335 (1994)). However, several of these studies address hematological disorders where genetic changes are assessed in freshly fixed smears from bone marrow aspirates or peripheral blood specimens. U.S. Pat. No. 6,573,043 describes combining morphological staining and/or immunohistochemistry (IHC) with fluorescence in situ hybridization "FISH" within the same section of a tissue sample.

U.S. Pat. No. 6,534,266 describes an in situ hybridization method for detecting and specifically identifying transcription of a multiplicity of different target sequences in a cell. The method includes assigning a different bar code to at least five target sequences, with each target sequence containing at least one predetermined subsequence. Each bar code contains at least one fluorochrome, and at least one bar code comprises at least two different, spectrally distinguishable fluorochromes. A probe set specific for each target sequence is provided in the method. Each probe set contains a hybridization probe complementary to each subsequence in the target sequence. Each probe is labeled with a fluorochrome, and the fluorochromes in each probe set collectively correspond to the bar code for the target sequence of that probe set. Similar techniques are envisioned in combination with the invention disclosed herein.

Further, although spotted chip expression microarrays have been used extensively to detect the presence or absence of multiple specific mRNAs simultaneously in tissue, to date the effective application of this technique has been limited to fresh frozen tissue and does not describe an easy application utilizing paraffin-embedded or other fixed-treated tissue (for example, see United States Patent Publication Nos. 20030040035 and 20020192702). Because much of the cell lines and tissue available for scientific or medical study has been fixed, the ability to effectively use spotted chip arrays on fixed-treated cell lines and tissue would be of great potential value in (1) the discovery of the molecular mechanisms of the cell and its surrounding tissue in health and disease, (2) the creation of tests diagnostic of disease, (3) the creation of treatments therapeutic for disease, and (4) the identification of agents that are toxic to cells. Therefore, the present invention fulfills a need in the art by providing, for example, a process termed "mRNA liberation in fixed treated tissue or 'MLIFFT'" to enable the detection of mRNA, especially pre-mRNA, in fixed treated tissue.

In this disclosure, we report the development of fluorescent in situ hybridization "FISH" protocols using cultured cells to yield expression profiles previously unobtainable by other methods (e.g., Levsky, J. M., et al. Science 297, 836 (2002); Kosman D., et al. Science, 305, 846 (2004)).

BRIEF DESCRIPTION OF THE INVENTION

As will be understood by one of skill in the art, in one aspect the present invention provides a method for rendering fixed treated cell-lines and tissue (i.e. paraffin embedded tissue) susceptible to further analysis using fluorescence detection methods. Such methods were formally not compatible with fixed treated cell lines or tissue. One aspect of this invention, therefore, provides a method and composition which will be useful in a range of protocols as will be apparent to one of skill in the art. While several of these protocols will be herein described, such description is not meant in any way to limit the applicability of the current invention.

In one aspect, the invention provides a method of autofluorescence reduction (also called sample preparation in this disclosure) in a sample during FISH. The process comprises treating the cell-lines or tissue with ammonia-ethanol and sodium borohydride and pressure cooking prior to performing FISH.

In one aspect, the invention provides a method, termed MLIFTT, to enable the detection of messenger RNAs, immature or premessenger RNAs, and nascent RNAs (i.e. those RNA transcripts still associated with engaged polymerases and chromosomes) in fixed-treated cell lines or tissue. The invention also describes the linkage of the MLIFTT process to enable the detection of one or more specific mRNAs in fixed-treated cell lines or tissue through the process of fluorescence in situ hybridization ("Tissue-FISH") with or without quantitative computational fluorescence microscopic analysis. Such linkage allows the use of fixed treated cells in the evaluation of toxicological or therapeutic responses to agents which were administered to the cells prior fixation. The invention also describes the linkage of the MLIFTT process to microarray analyses using fixed-treated cell lines or tissue. The invention also describes the linkage of the MLIFTT process to enable other potential measurements.

In one aspect, the invention provides a process to treat cell lines or tissue for the specific purpose of detecting RNA transcripts. The process comprises treating the cell lines or tissue with ammonia-ethanol and sodium borohydride and pressure cooking the cell lines or tissue to achieve improved detection of RNA transcripts. Without being bound by theory, it is thought that the chemical treatments reduce the autofluorescence of the cell lines or tissue and the physical treatments overcome interference created by the fixative-induced chemical bonds.

In another aspect, the invention combines a method to pre-treat the cell lines or tissue with advances in computational fluorescence microscopy with specialized probes designed to visualize expression of one or many genes (i.e., detecting one or many mRNAs, pre-mRNAs, and nascent RNAs) simultaneously inside single cells (either alone or within a tissue such as, for example, in paraffin embedded tissue). Single-cell expression profiling is valuable because it enables the simultaneous detection of the presence (or absence) of multiple molecular entities or "markers" within the cell. The presence (or absence) of these molecular entities characterizes and provides insight into the regulatory activity of each cell. The detection of these entities has potential value in (1) the discovery of the molecular mechanisms of the cell and its surrounding tissue in health and disease, (2) the creation of tests that are diagnostic of disease, (3) the identification of agents that are therapeutic for disease, and (4) the identification of agents that are toxic to cells.

In another aspect, the invention provides a process combining the pre-treatment of the cell lines or tissue by chemical and physical processes followed by the detection of specific pre-mRNA transcript(s) through specific fluorochrome-labeled oligo-probes ("Tissue-FISH"). The pre-treatment process is the treatment of the cell lines or tissue with ammonia-ethanol and sodium borohydride and pressure cooking the cell lines or tissue. Following the treatment, specific probes are applied to the cell lines or tissue to detect specific pre-mRNA transcripts. The specific probes, labeled with fluorochromes, can be detected manually or by quantitative computational fluorescence microscope analysis. In this way, multiple specific pre-mRNA entities may be detected in a single cell. The limit of the number of specific pre-mRNA entities is limited only by the number of unique available fluorochromes that can be attached to these probes.

In another aspect, the invention provides a pre-mRNA labeling technique that can increase the number of molecular entities that may be simultaneously detected beyond the number of uniquely (or spectrally distinct) available fluorochromes. This feature of the invention is to create and apply multiple oligo-probes to the cell lines or tissue which are specific for a pre-mRNA transcript that, when attached to their target pre-mRNA, create a unique combinations of fluorescent probes (the combination is referred to herein as a "barcode") for each transcript. These barcodes can then be detected using quantitative computational fluorescence microscopic analysis. The number of potential RNA transcripts (mRNA, pre-mRNA, and nascent RNA) that can be simultaneously detected has been increased from the number of available unique fluorochromes ("n") to n raised to the power of the number of fluorochrome-unique probes that can be created for a specific pre-mRNA.

In another aspect, the invention provides a method to quantify the level of specific RNA transcript expression by using a computerized detection system to quantify the level of attached fluorochrome labeling by measuring the intensity of the fluorochrome signal. The level of specific pre-mRNA expression is calculated by assuming it is proportional to the level of intensity of the fluorochrome signal.

In another aspect, the invention includes a process of combining the pre-treatment of the fixed-treated cell lines or tissue by chemical and physical processes followed by the detection of specific RNA transcript(s) through spotted chip arrays. The pre-treatment process is the treatment of the cell lines or tissue with ammonia-ethanol and sodium borohydride and pressure cooking the cell lines or tissue. Following this pre-treatment of the fixed-treated cell lines or tissue, the cell lines or tissue is disrupted and then applied to spotted chip arrays to detect the presence and level (or absence) of specific RNA transcripts.

In yet another aspect, the invention provides a process of measuring the presence or absence or quantified amount of specific RNA transcripts using probes to detect these entities in (i) cell lines or (ii) cell lines or tissue from animals or (iii) cell lines or tissue from humans, to determine if the respective cell lines or tissue, when treated with a test compound, displays a gene expression profile indicating a potential therapeutic or toxic activity for the test compound. Such effects would be revealed by differences in pre-mRNA or mRNA expression between the treated and untreated cell lines or tissue. Probes can be designed, for example, to specifically target known therapeutic or toxicologic pathways. This process could be conducted on culture cell lines or fresh frozen cell lines or tissue or fixed cells or fixed tissue. If this process is conducted on fixed cells or fixed tissue, the MLIFTT process could be employed to liberate the pre-mRNA or mRNA for measurement. FISH applied to cell lines or Tissue-FISH applied to cell lines could be used to enable the measurement of the pre-mRNA or mRNA. To make the measurement more effective and valuable, multiplexed FISH applied to cell lines or Tissue-FISH could be used to measure multiple pre-mRNAs or mRNAs simultaneously in the same sample of cell lines or tissue. This would be more valuable because it 1) more efficiently uses potentially scarce cell lines and tissue as well as expensive reagents, 2) saves time, and 3) allows investigators to see the simultaneous interrelationships of gene expression more clearly in single cells or groups of cells.

One embodiment of the invention is directed to a method of in situ hybridization to detect nascent RNA species in a tissue sample. In the first step, autofluorescence reduction is performed on the tissue sample. In a preferred embodiment, the tissue sample is mounted on a slide (e.g., glass slide) for easier manipulation. In the second step, at least one nucleic acid probe specific for a species of nascent RNA is hybridized to the tissue sample. In the third step, the location of the at least one nucleic acid probe is detected to determine the presence of the nascent RNA.

The method of the invention provides considerable advantage in resolution over the current art because it is capable of determining the location of the nascent RNA or any fluorescent signal such as the signal of a chromosome probe to within 50 microns, within 40 microns, within 30 microns, 20 microns or within 10 microns. This resolution allows pinpointing the nascent RNA to a location within the nucleus. In fact, the methods of the invention have sufficient resolution to determine at least 10,000 locations in the nucleus and locate the nascent RNA to one of these locations. In a preferred embodiment, the method can locate the nascent RNA to one of at least 20,000 locations in the nucleus, to one of at least 30,000 locations in the nucleus, to one of at least 40,000 locations in the nucleus or to one of at least 50,000 locations in the nucleus. These values are based on a nucleus of approximately 10 microns in diameter. Obviously, the number of locations in a nucleus would increase for cells with bigger nucleus or decrease for a cell with a smaller nucleus.

Another advantage of the invention's method is that it can be used on a wide variety of samples including cultured cells, fixed treated tissues of any age (from freshly made fixed tissue to tissues fixed over 10, over 20, over 30, over 40 or over 60 years old. The tissue sample may be stained, such as hematoxylin and eosin (H&E) stained or the tissue may be previously stained but destained. The tissue sample may also be a paraffin embedded tissue sample, a frozen sample, cells which have been placed on a slide by centrifugation (i.e., cytospin (Thermo Electron Corporation, Waltham, Mass. USA), or a sample on a slide. Some sample may have a combination of the above listed characteristics. For example, a fixed tissue may be paraffin embedded and H&E stained and destained. Such samples are also suitable as a starting material for the methods of the invention.

The methods of the invention are particularly suitable for the detection of nascent RNA (also called nascent transcripts)

for the diagnosis of neoplastic or preneoplastic tissues. Preneoplastic tissues would include tissues which has a high probability to turn cancerous. These tissues include, for example, tissue with hyperplasia and hypertrophy.

Sample preparation (autofluorescence reduction) may be performed by pressure cooking the tissue sample to produce a pressure cooked sample and then treating the sample with ammonia ethanol and sodium borohydride. For example, a tissue may be pressured cooked, then contacted with ammonia ethanol, and then contacted with sodium borohydride. Contacting may be performed, by dipping a slide containing the tissue sample into a container containing ammonia ethanol and then dipping the slide into a container containing sodium borohydride.

Pressure cooking may be performed, for example, by incubating a glass slide with sections of the sample tissue in a chamber at about 125° C., at a pressure of between about 20 to about 24 PSI. This can be performed in a commercially available decloaking chamber or other chamber that can maintain these conditions. During pressure cooking, the sample tissue may be contacted with a solution that has deparaffinization and/or antigen retrieval activities. Examples of such solutions include, for example, "Declere™" solution from Cell Marque (Hot Springs, Ariz., USA) or "Reveal™" solution from BioCare Medical (Concord, Calif., USA). Under these conditions, pressure cooking may be performed for between 10 minutes and 1 hour such as, for example, for 30 minutes.

Following pressure cooking, the sample may be contacted to ammonia-ethanol. For example, the sample may be dipped in a tank of ammonia-ethanol. The ammonia-ethanol may be at a concentration of about 0.1% to 0.5%. In a preferred embodiment, the ammonia-ethanol may be about 0.25%. The length of contact may be between about 10 to 50 minutes, between 10 to 30 minutes or about 40 minutes.

Following ammonia-ethanol treatment, the sample may be treated by contact with sodium borohydride at a concentration of about 1% to about 5%. This contact may last between 10 and 50 minutes such as, for example, for about 20 minutes.

The ammonia-ethanol treatment and the sodium borohydride treatment may be performed in any order. So for example, after pressure cooking, the tissue sample may be contacted first with sodium borohydride followed by contact with ammonia-ethanol second. Alternatively, after pressure cooking, the tissue sample may be contacted first with ammonia-ethanol followed by contact with sodium borohydride.

Any nascent RNA may be detected by the methods of the invention. In particular, nascent RNA detected by the methods of the invention may be transcribed from genes such as the following: GalNAc-T3 (UDP-N-Acetyl-alpha-D-galactosamine transferase); Prostate-Specific Membrane Antigen (PSMA); Hepsin (transmembrane protease, serine1); Differential Display Code 3/Prostate Cancer Antigen 3 (DD3/PCA3); B-cell Lymphoma 2 gene (BCL2); BCL2-related protein gene (BCLx1); Clusterin; Heat Shock Protein 27-kDa (Hsp27); androgen receptor (AR); wingless-type MMTV integration site family member 5A (Wnt5a); Kruppel-like factor 6 (KFL6); Etoposide induced 2.4 mRNA (Ei24/SSR1); Erythrocyte protein band 4.9 (EPB 4.9); Mitogen-activated protein kinase 4 (Map4K4); Estrogen Receptor Alpha (ER alpha); phosphatidylinositol 4-kinase (PIK4); Desmin; Vimentin; and/or Beta 2 microglobulin (B2M).

The hybridization step of the method may involve the use of between 8 to 82 probes for each nascent RNA species detected. Thus, for example, if two nascent RNA species are detected, the total number of probes may be between 16 to 164 (i.e., 8 to 82 probes for each nascent RNA).

Each of the probes in the methods of the invention may be attached to one or more fluorescent moieties. These fluorescent moieties may include FITC, Cy3, Cy3.5, Cy5, Cy5.5, DAPI or a combination of these moieties.

Of the 8 to 82 probes used for the detection of one species of nascent RNA should contain a unique combination of fluorescence moieties. For example, if two nascent RNA, A and B, are to be detected, the probes for nascent RNA A may contain the fluorescent moieties Cy3 and Cy3.5 while the probes for nascent RNA B may contain the fluorescent moieties Cy3.5 and Cy5. Thus, the fluorescent moieties (Cy3 and Cy3.5) used to detect nascent RNA A would have a different combination than that for nascent RNA B (Cy3.5 and Cy5).

The optimal probe size is between 25 to 1000 bases in length. In a preferred embodiment, the probe size between 40 and 60 bases such as about 50 bases. Each of the probes is specific for a region of the nascent RNA. The region may be part of an exon, part of an intron or a combination of both exon and intron sequences. Furthermore, the region may be a 5' untranslated region or a 3' untranslated region of a nascent RNA.

To improve analytical ability and to correlate the results of the methods with morphology, the tissue samples may be restained, for example, with H&E, after the detecting step.

Furthermore, the probes used in the hybridization step may include one or more probes specific for one chromosome or a fragment of a chromosome (e.g., the P arm of chromosome 12). Thus, during the detection of nascent RNA signal, a chromosome signal may also be detected. The colocalization of chromosome specific probes with nascent RNA specific probes would indicate that the nascent is expressed (transcribed) from that chromosome (see FIG. 2B and legends).

The methods of the invention, by detecting the expression of nascent RNA, may be used to diagnose a disorder—by detecting the expression of nascent RNA and mRNAs expressed from genes usually associated with a disorder. The disorders may be, at least, a neoplastic (cancer) disorder or a preneoplastic (pre-cancer) disorder. These disorders may include, at least, prostatic cancer or prostatic intraepithelial neoplasia. The nascent RNAs that could be detected by the methods of the invention include, as least, oncogenes, anti-oncogenes and the like.

Another advantage of the invention is that nascent RNA detection is compatible with existing chromosome detection methods. The detection of chromosomal location may be performed at any time before, after or during the nascent RNA FISH detecting procedure. For example, chromosome specific probes may be hybridized and detected before application of nascent RNA probes. Alternatively, chromosome specific probes may be hybridized at the same time with nascent RNA probes and the subsequent washing and detection step may be performed together. In this case, the chromosome specific probe ideally should have a similar hybridization characteristic as the nascent RNA probes. Further, chromosome location may be performed after nascent RNA detection. As a further example, chromosome probes and nascent RNA probes may be applied together and detected at separate steps, or chromosome specific probes and nascent RNA probes may be applied separately and detected at the same step. The two probe types (chromosome probe(s) or nascent probe(s)) are compatible and it is not necessary to strip one type of probe from the tissue sample before the use of the other. Any detection method used to detect nascent RNA probes may also be used to detect chromosomal location.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 7 depict the prostate gland of FIG. 6, treated with the sample preparation methods of the invention and probed with the pet-FISH method of the invention. Expression of AR is clearly seen.

DETAILED DESCRIPTION OF THE INVENTION

Figure 1:
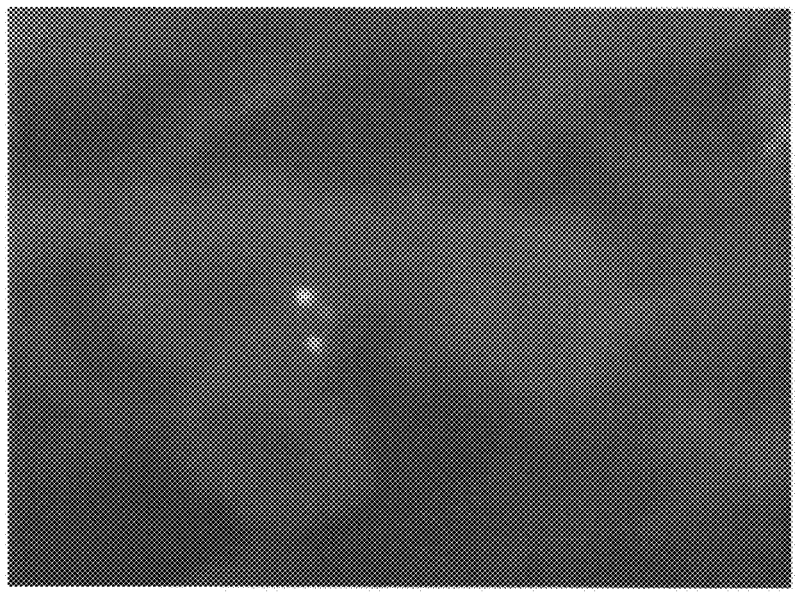
FIG. 1: Detection of SMG-1 gene on Paraffin-embedded prostate Carcinoma using Cy3 and Cy5 labeled probe (arrows are pointing at two transcription sites).
Figure 2A:
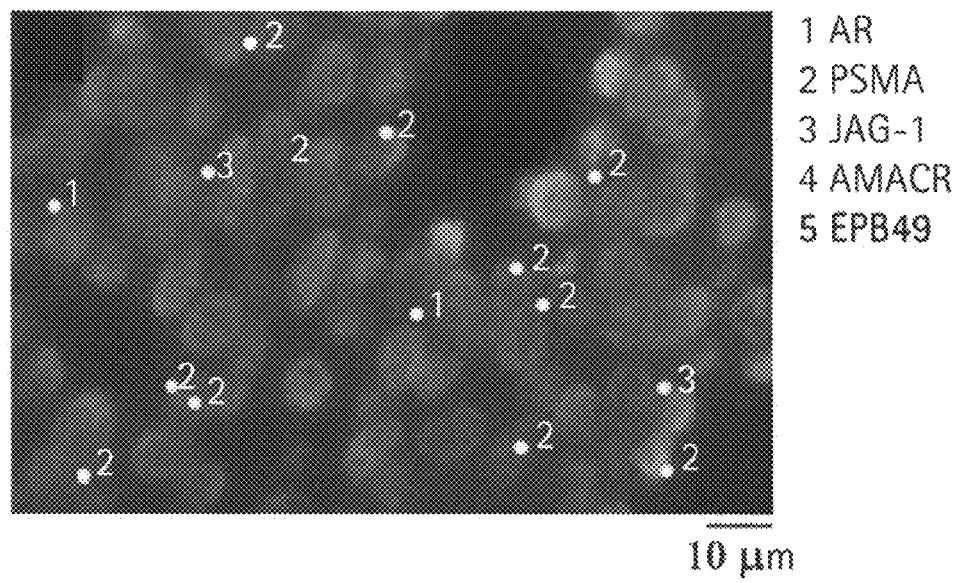
FIG. 2 depicts multiplex detection of five genes in cancer cells. (A) FFPE section of a prostate tumor PCa (1982 archive) with peT-FISH, demonstrating restricted expression of 4 genes to the epithelial cells of the tumor annotated with the automated transcription site finder. The 5th gene in the barcoding scheme, EPB4.9, was only rarely detected and is not identified in this particular field. (B). Colocalization of a gene and its chromosome. FFPE PCa exhibiting the co-localization of a DNA locus-specific probe for the chromosome containing the Androgen Receptor (AR, red spots) with the AR peT-FISH on a single section (green spots). (C-E) Correlation of single cell multi-gene expression profiles with diagnostic pathology. Hematoxylin and Eosin stained images of focal PIN (C), PCa (D) and PCaMet (E) respectively, superimposed with the gene expression data from peT-FISH analyses of 3 genes (PSMA, AR and JAG-1) obtained from the slide after destaining (Bars are 10 µm).
FIGS. 2I, 2K and 2L are lower magnification views of FIGS. 2C, 2D and 2E respectively.
FIG. 2J is the fluorescent view of FIG. 2C with the location of various nascent RNA annotated.
FIG. 2F depicts the diagnostic value of gene expression profiling. Five genes quantitated in prostate tissue samples indicate that a gene expression "fingerprint" can be associated with a specific diagnosis using t-tests. Values with an asterisk represent statistically significant combinatorial components for each differential diagnosis. The pairings are presented that represent the significant combinatorial components for each differential diagnosis. (p values in red).
FIG. 2G depicts the gene expression patterns of each diagnosis as a function of each gene. (H). The gene expression patterns characteristic of each diagnosis (focal PIN, PCa, PCaMet and Benign).
Figure 2B:
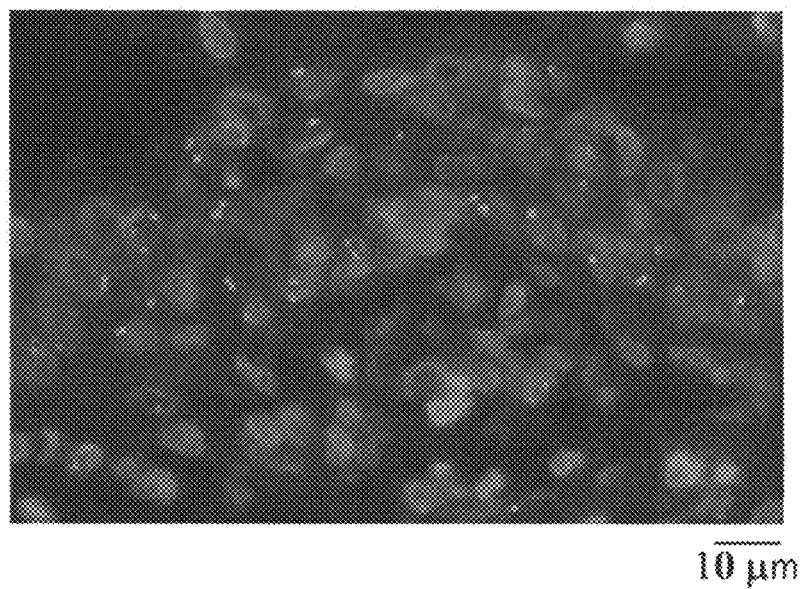
Figure 2C:
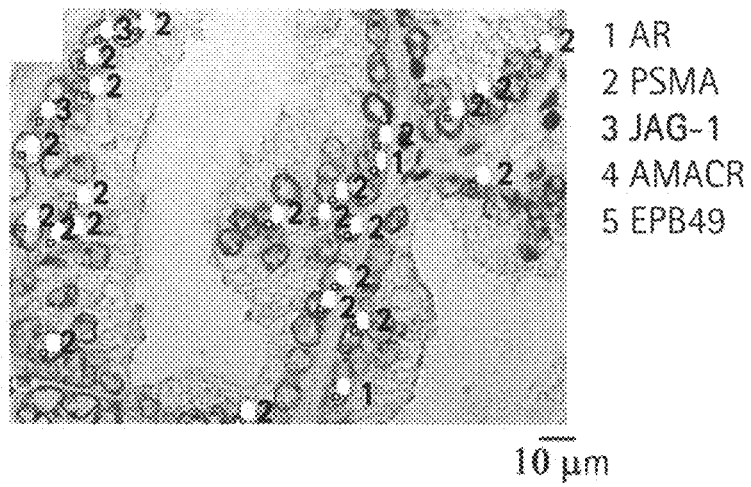
Figure 2D:
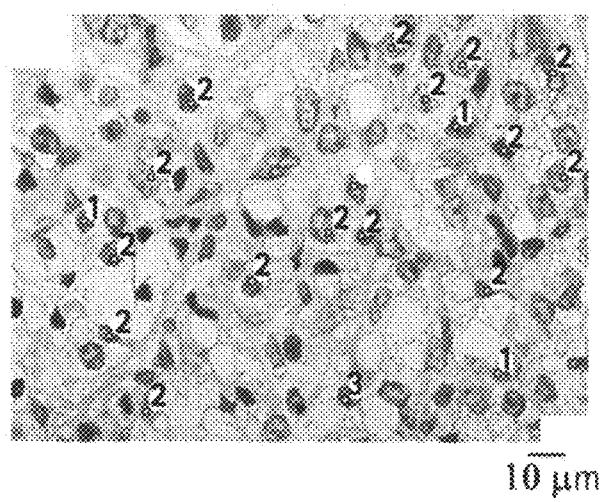
Figure 2E:
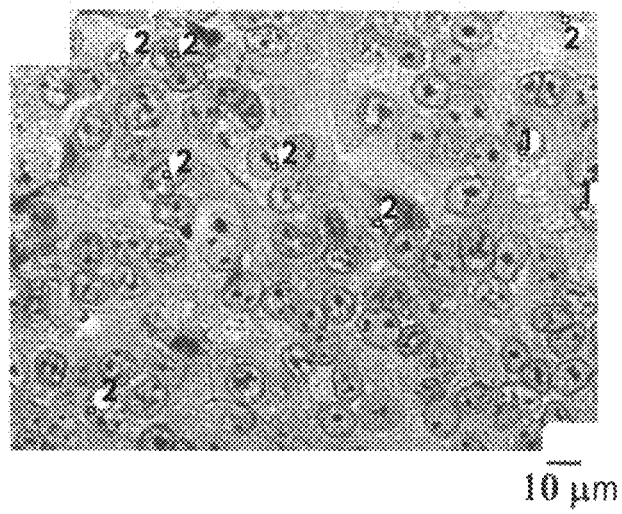
Figure 2I:
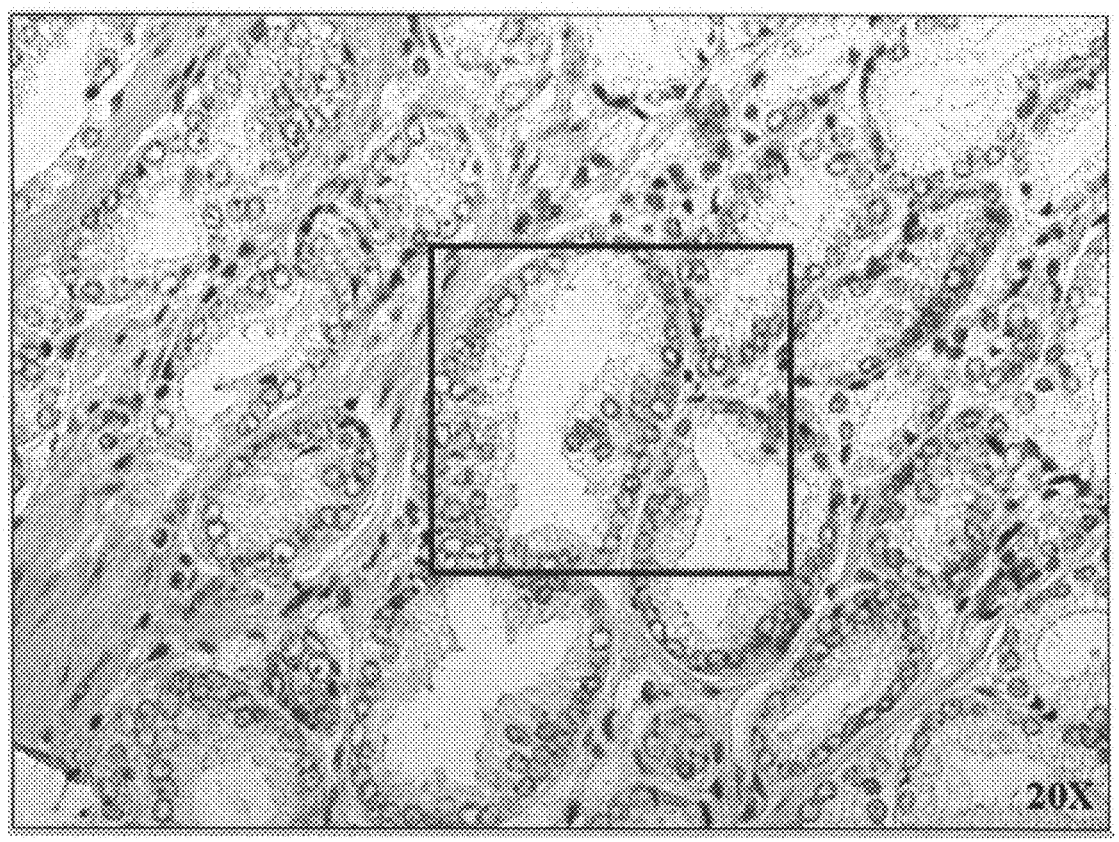
Figure 2J:
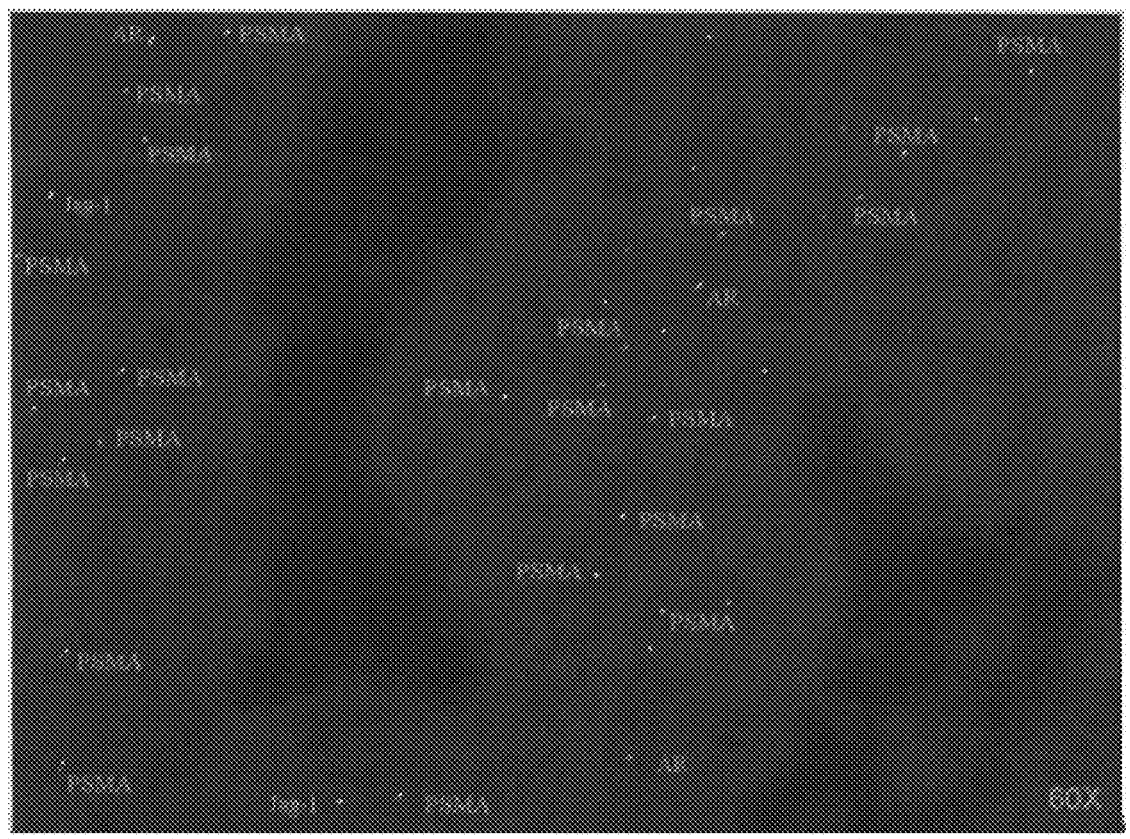
Figure 2K:
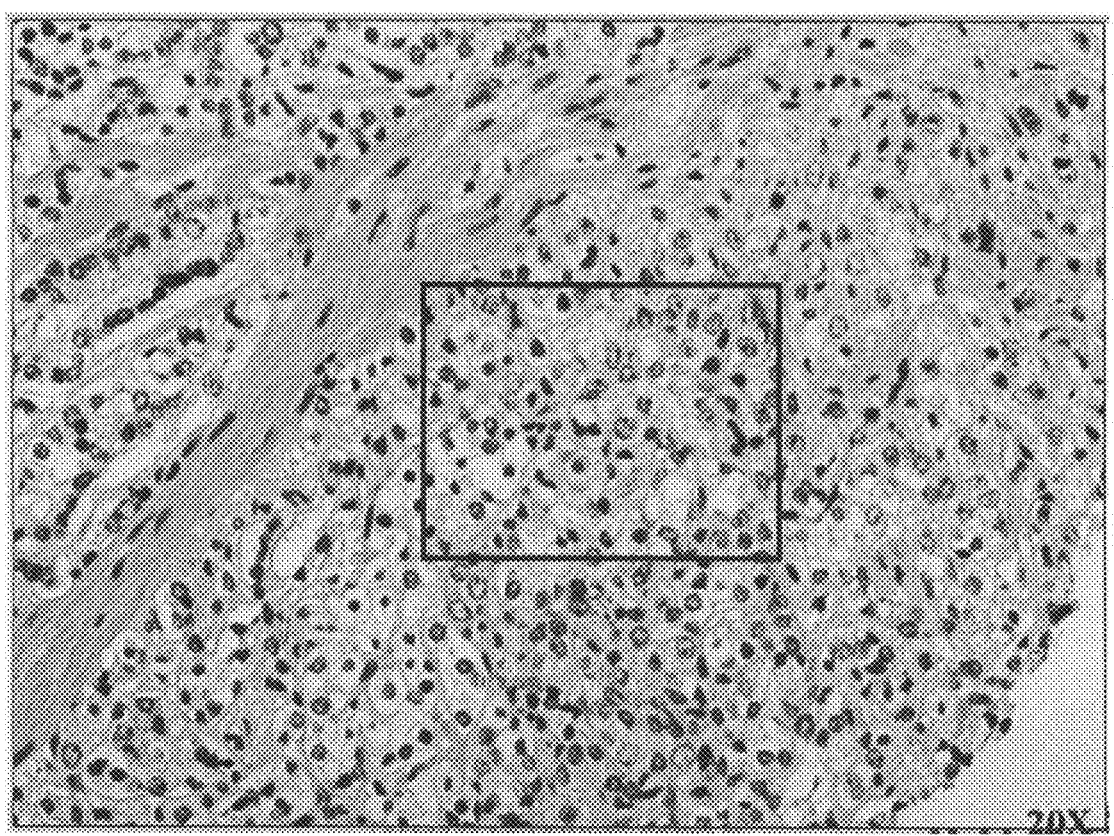
Figure 2L:
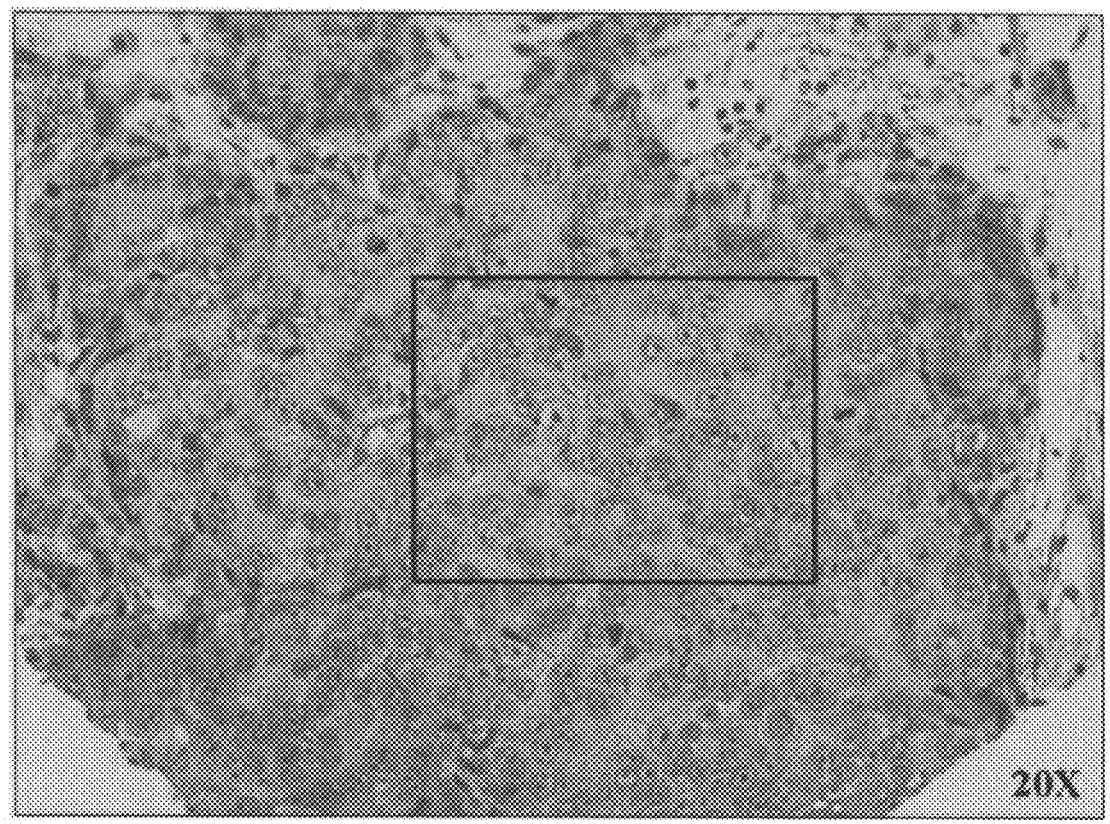
Figure 3A:
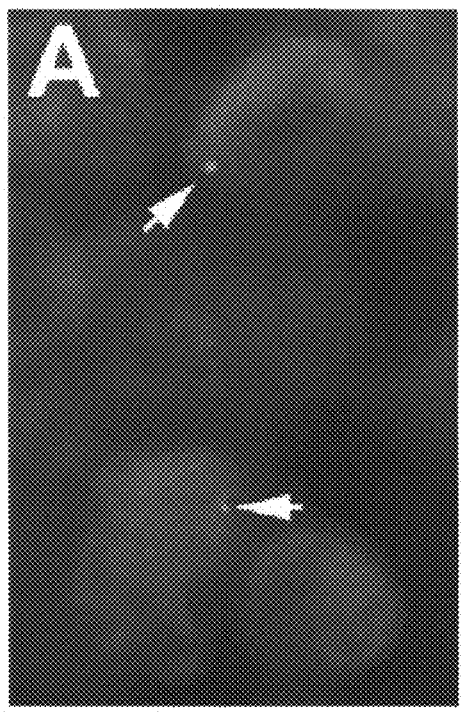
FIG. 3 depicts a series of photographs showing detection of nascent RNA (transcription sites) in paraffin embedded tissue. (a) Detection of SMG-1 (8 probes) transcription sites (arrows) in human prostate carcinoma. (Bar is 5 µm). (b) Detection of SMG-1 (41 probes) nascent transcripts (arrows) in human prostate carcinoma. (Bar is 5 µm). (c) Colocalization of a gene and its chromosome. Prostate carcinoma exhibiting the co-localization of a DNA locus-specific probe for the Androgen Receptor (AR, red spots) with the AR peT-FISH on a single section (green spots). (Bar is 10 µm). (d) Multiplex detection of five genes in prostate cancer, (1982 archive) demonstrating restricted expression of 4 genes to the epithelial cells of the tumor annotated with the automated transcription site finder algorithm. The 5th gene in the barcoding scheme, EPB4.9, was only rarely detected and is not identified in this particular field (Bar is 10 µm).
Figure 3B:
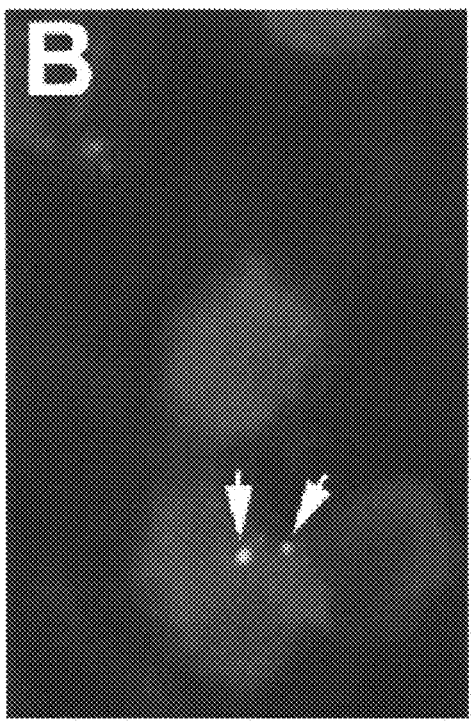
Figure 3C:
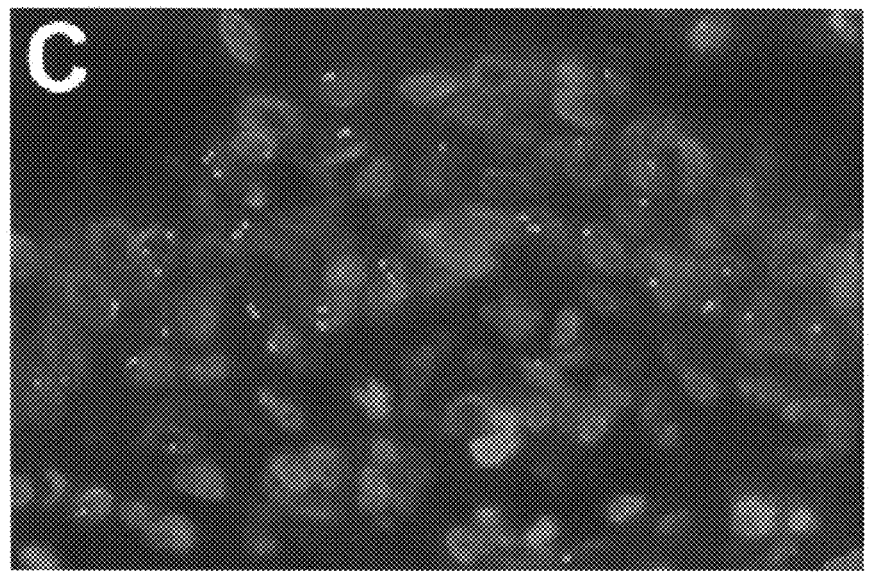
Figure 3D:
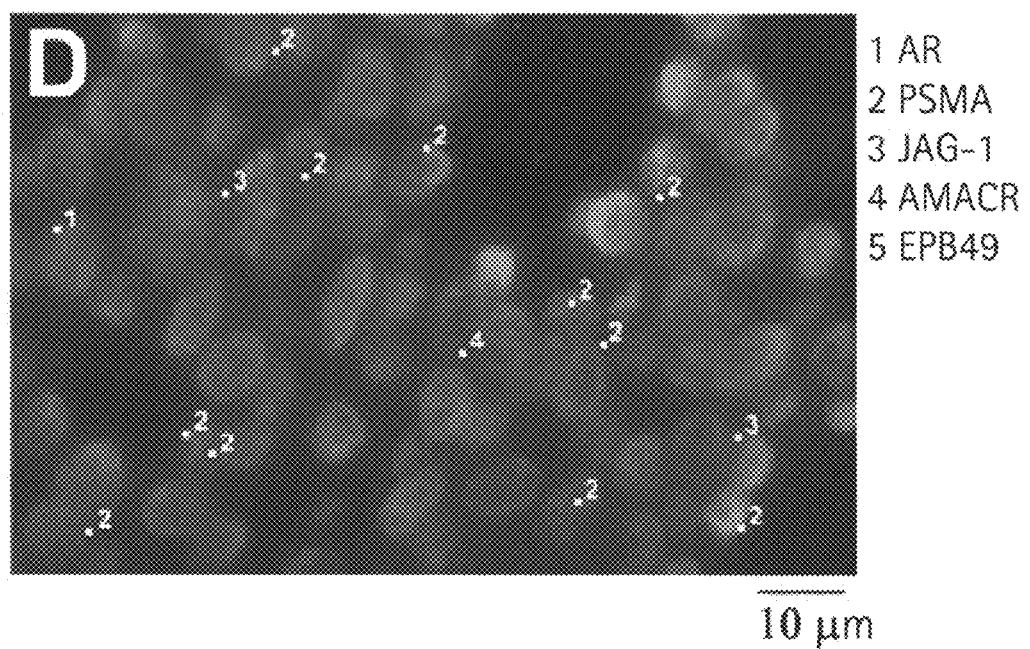

It is understood that this invention is not limited to the particular methodology, protocols, cell lines, animal species or genera, constructs, and reagents described which may be modified or substituted as would be known to one of skill in the art. Further, the terminology of this specification is for the purpose of describing particular embodiments only, and is not intended to limit the scope of the present invention.

In this disclosure, the singular forms "a", "and", and "the" include plural referents unless the context clearly dictates otherwise. Thus, for example, a reference to "a probe" includes reference to one or more probes and equivalents thereof known to those skilled in the art. Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

In one aspect the present invention provides a method for rendering fixed treated cell-lines and tissue (i.e. paraffin embedded tissue) susceptible to further analysis using fluorescence detection methods. Such methods were formally not compatible with fixed treated cell lines or tissue. This invention, therefore, provides a method and composition which will be useful in a range of protocols as will be apparent to one of skill in the art. While several of these protocols will be herein described, such description is not meant in any way to limit the applicability of the current invention.

The present invention is directed, in part, towards improved methods for directly detecting the presence of a target nucleic acid in cells of paraffin-embedded or otherwise fixed-treated cell lines or tissue, a process termed "mRNA liberation in fixed-treated tissue or 'MLIFTT.' It is understood that MLIFTT is applicable to the detection of all transcript RNAs in a cell including mRNA, pre-mRNA, and nascent RNA. More specifically, novel improvements of the traditional fixative/pretreatment methods are described which employ treatment of the tissue with ammonia-ethanol and sodium borohydride and pressure cooking the tissue to achieve improved detection of pre-mRNA.

"Tissue-FISH" refers to the use of fluorescent labeled probes, for example, of between 20 to 100 bases in the detection of nucleic acids in paraffin embedded tissue samples. In one preferred embodiment, the labeled probe is about 50 bases in length.

In this disclosure, references to "tissue" and "sample tissue" are applicable to all tissues including frozen sections and paraffin embedded tissues. Further, "tissue" and "sample tissue" also encompass cell lines, including cell lines that are analyzed as individual cells or as paraffin embedded cells. Accordingly, although one term may be used with respect to a particular method, it should be understood that the composition or method applies equally to the other. In referring generally to the types of material that may be utilized according to the invention, the inventors may use terms like "sample" etc. It is understood that sample may refer to individual cells, cell lines, tissue sections (including frozen sections or paraffin embedded sections) and the like.

As used herein, "fluorochrome" refers to a particular fluorescent dye, e.g., Cy3, Cy5, without regard to number of individual dye molecules, and without regard to chemical conjugation. The term "fluorophore" refers to an individual fluorescent dye molecule or conjugated moiety.

As used herein, the term "nucleic acid" refers to DNA, RNA, or the equivalent thereof, including pre-mRNA, hnRNA, mRNA, nascent RNA, cDNA, chromosomal, mitochondrial, viral and/or bacterial nucleic acids. It is also understood that RNA may belong to more than one descriptive name above. For example, hnRNA encompasses pre-mRNA. The term "nucleic acid" encompasses either or both strands of a double stranded nucleic acid molecule and includes any fragment or portion of an intact nucleic acid molecule.

As used herein, the term "probe" refers to synthetic or biologically produced nucleic acids that are engineered to contain specific nucleotide sequences which hybridize under stringent conditions to target nucleic acid sequences.

As used herein, a "labeled probe" is defined as a probe which is prepared with a marker moiety for detection. The marker moiety is attached at either the 5' end, the 3' end, internally, or in any possible combination thereof. That is, one probe may be attached to multiple marker moieties. The preferred moiety is an identifying label such as a fluorophore. The labeled probe may also be comprised of a plurality of different nucleic acid sequences each labeled with one or more marker moieties. Each of the marker moieties may be the same or different. It may be beneficial to label the different probes (e.g., nucleic acid sequences) each with a different marker moiety. This can be accomplished by having a single distinguishable moiety on each probe. For example, probe A may be attached to moiety X and probe B may be attached to moiety Y. Alternatively, probe A may be attached to moieties X and Y while probe B may be attached to moiety Z and W. As another alternative, probe A may be attached to moieties X and Y while probe B may be attached to moieties Y and Z. All the probes "A" and "B" described above would be distinguishable and uniquely labeled.

By "subject" or "patient" is meant any single subject for which therapy is desired, including humans, cattle, horses, pigs, goats, sheep, dogs, cats, guinea pigs, rabbits, chickens, insects and so on. Also intended to be included as a subject are any subjects involved in clinical research trials not showing any clinical sign of disease, or subjects involved in epidemiological studies, or subjects used as controls.

"Toxicology analysis" as used herein refers to protocols directed towards identifying, for example, genetic expression (or lack thereof) indicative of a toxic response by the cell to, for example, an agent. Toxicological response pathways are familiar to those of skill in the art.

By "tissue sample" is meant a collection of similar cells obtained from a tissue of a subject or patient, preferably containing nucleated cells with chromosomal material. The four main human tissues are (1) epithelium; (2) the connective tissues, including blood vessels, bone and cartilage; (3) muscle tissue; and (4) nerve tissue. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. The tissue sample may contain compounds which are not naturally intermixed with the tissue in nature such as preservatives, anticoagulants, buffers, fixatives, nutrients, antibiotics, or the like. In one embodiment of the invention, the tissue sample is "non-hematological tissue" (i.e. not blood or bone marrow tissue).

For the purposes herein a "section" of a tissue sample is meant a single part or piece of a tissue sample, e.g. a thin slice of tissue or cells cut from a tissue sample. It is understood that multiple sections of tissue samples may be taken and subjected to analysis according to the present invention, provided that it is understood that the present invention comprises a method whereby the same section of tissue sample is analyzed at both morphological and molecular levels, or is analyzed with respect to both protein and nucleic acid.

As used herein, "cell line" refers to a permanently established cell culture that will proliferate given appropriate fresh medium and space.

By "correlate" or "correlating" is meant comparing, in any way, the performance and/or results of a first analysis with the performance and/or results of a second or further analysis. For example, one may use the results of a first analysis in carrying out the second analysis and/or one may use the results of a first analysis to determine whether a second analysis should be performed and/or one may compare the results of a first analysis with the results of a second analysis. With respect to the embodiment of morphological analysis followed by FISH, one may use the results obtained upon morphological staining to determine area(s) of a tissue section which are normal and/or area(s) which are cancerous. Thus, histological normal area(s) in a heterogeneous tumor biopsy may be used as internal normal control(s).

By "gene" is meant any nucleic acid sequence or portion thereof with a functional role in encoding or transcribing a protein or regulating other gene expression. The gene may consist of all the nucleic acids responsible for encoding a functional protein or only a portion of the nucleic acids responsible for encoding or expressing a protein. The nucleic acid sequence may contain a genetic abnormality within exons, introns, initiation or termination regions, promoter sequences, other regulatory sequences or unique adjacent regions to the gene.

By "genetic abnormality" is meant a deletion, substitution, addition, translocation, amplification and the like relative to the normal native nucleic acid content of a cell of a subject.

By "disease gene" is meant a gene that results in altered protein product (i.e., protein different from native protein in terms of sequence, structure and/or amount expressed) and results in a disease or associated with a disease profile.

By "deletion" is meant the absence of all or part of a gene.

By "amplification" is meant the presence of one or more extra gene copies in a chromosome complement.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

The term "fluorescent labeled nucleic acid probe" refers to a probe comprising (1) a nucleic acid sequence tagged with a fluorescent dye (2) capable of hybridizing with a target nucleic acid sequence.

By "morphological stain" is meant a dye that stains different cellular components, in order to facilitate identification of cell type and/or disease state by light microscopy. Preferably, the morphological stain is readily distinguishable from any label used in the FISH analysis, e.g., a stain which will not autofluorescence at the same wavelength as the fluorochrome used in the FISH analysis.

The novel and unique fluorescence in situ hybridization and detection technique described herein is a method which allows the use of recombinant DNA or RNA probes with paraffin-embedded or otherwise fixed-treated samples, including for example, cells, microorganisms, or tissue sections, and is compatible with microscopic examination routinely performed in bacteriology, parasitology, histology or pathology laboratories. The present invention applies a nucleic acid probe of predetermined nucleotide sequence to the sample cells or tissue and to the examination of the sample by microscopy, for example, to determine which cells or tissues within the population contain the specific nucleic acid target sequences of interest.

1. Sample Preparation Fixing and Paraffin Embedding Tissue

The methods of this invention are suitable for use with any specimen obtained from a patient including but not limited to, whole blood, serum, plasma, sputum, urine, breast milk, cerebral spinal fluid, breast, prostate, ovary, colon, lung, endometrium, stomach, salivary gland, pancreas and other tissue. The tissue sample can be obtained by a variety of procedures including, but not limited to surgical excision, aspiration or biopsy. The tissue may be fresh or frozen. In one embodiment, the tissue sample is fixed and embedded in paraffin or the like. The methods of the invention are also suitable for detection of a pathogen within the cells of an insect vector.

In a preferred embodiment, the sample is deposited onto the slide by standard means, and is then fixed onto the slide. The purpose of fixing cells or tissue is to preserve the morphology of the cells or tissue such that RNA is retained within the cellular matrix under the rigorous conditions experienced during in situ hybridization. The preferred method thus utilizes a fixative which is able to preserve and retain nucleic acids of the cell and at the same time cross-link and/or precipitate the proteins in the cellular matrix such that the cell or tissue remains substantially in open configuration for probe penetration and subsequent hybridization.

One advantage of the methods of the invention is that fixation may be performed by conventional methodology (See e.g., "Manual of Histological Staining Method of the Armed Forces Institute of Pathology," 3rd edition (1960) Lee G. Luna, HT (ASCP) Editor, The Blakston Division McGraw-Hill Book Company, New York; The Armed Forces Institute of Pathology Advanced Laboratory Methods in Histology and Pathology (1994) Ulreka V. Mikel, Editor, Armed Forces Institute of Pathology, American Registry of Pathology, Washington, D.C.). One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a tissue sample.

Fixation may be performed in a number of ways including fixation by cross-linking, fixation by precipitation, and fixation by freezing (cryofixation). Cryofixation involves rapidly freezing the cells or tissues on a cooled block of heat-conductive metal or rapid plunging into a cold medium, such as liquid nitrogen or freon. Following freezing, the samples may then be treated with a cross-linking reagent, discussed below, in a process called 'freeze substitution'.

Fixation by cross-linking is a method commonly used for fluorescence microscopy. It involves treating specimens with reagents that penetrate into the cells and tissues and form covalent cross-links between intracellular components. The most commonly used cross-linking agents are aldehydes, which form covalent bonds between adjacent amine-containing groups through Schiff acid-base reaction. These bonds form both inter- and intra-molecularly and are, therefore, very effective fixatives for proteins and nucleic acids. The two most frequently used aldehydes are formaldehyde and glutaraldehyde. Both fixatives have advantages and disadvantages, which will be discussed below. Other aldehydes, such as acrolein, have been used historically, but do not preserve samples as well.

Glutaraldehyde is a four carbon molecule terminated at both ends by aldehyde groups. It is an extremely efficient fixative, and is widely used by light and electron microscopy for its efficacy in preserving cellular structure. Use of glutaraldehyde does have certain disadvantages, however. First, its comparatively high molecular weight limits its ability to diffuse into thick specimens, such as tissue sections or embryos. This is further exacerbated by the fact that as the tissue is cross-linked by the fixative, its ability to penetrate over time diminishes. For such samples, formaldehyde may be a better option. Second, free aldehyde groups fluoresce efficiently at the same wavelengths as many of the fluorescent probes employed by biologists. As glutaraldehyde possesses two functional groups per molecule, background autofluorescence may be a significant problem in fixed tissues, effectively lowering the probe's signal to noise. This problem may be circumvented by using relatively low concentrations of glutaraldehyde (i.e. less than 1%). Unreacted aldehydes may also be quenched by treating fixed samples with reducing agents, such as sodium borohydride, to reduce free aldehyde groups to alcohols, or by reacting them with exogenous amine-containing reagents, such as ammonium chloride or glycine. In a preferred embodiment of the present invention, the fixed tissue is treated with sodium borohydride to quench autofluorescence.

Formaldebyde is probably the most commonly used cross-linking fixative for biological samples. It has a single aldehyde-containing carbon and exists as a gas. Formaldehyde does not cross-link as effectively as glutaraldehyde, and for this reason is rarely used by-itself for electron microscopy. However, its small molecular weight allows it to penetrate cells and tissues rapidly, making it a choice fixative for thicker samples and autofluorescence of unreacted aldehyde groups is not usually a problem.

The selection of a specific fixation protocol will be dictated by several factors. First, the fluorescent probe to be used may place restrictions on which treatment may be necessary (i.e. some fixations prevent binding of certain dyes). Second, the size or thickness of a given sample may preclude the use of certain fixatives due to permeability (i.e. a fixative that is unable to penetrate into thick samples will only preserve the outer layers).

Generally, the fixed tissue is then dehydrated through an ascending series of alcohols, infiltrated and embedded with paraffin or other sectioning media so that the tissue sample may be sectioned. Alternatively, one may section the tissue and fix the sections obtained. By way of example, the tissue sample may be embedded and processed in paraffin by conventional methodology (See e.g., "Manual of Histological Staining Method of the Armed Forces Institute of Pathology", supra). Examples of paraffin that may be used include, but are not limited to, Paraplast, Broloid, and Tissue may. Once the tissue sample is embedded, the sample may be sectioned by a microtome or the like (See e.g., "Manual of Histological Staining Method of the Armed Forces Institute of Pathology", supra). By way of example for this procedure, sections may range from about three microns to about five microns in thickness. Once sectioned, the sections may be attached to slides by several standard methods. Examples of slide adhesives include, but are not limited to, silane, gelatin, poly-L-lysine and the like. By way of example, the paraffin embedded sections may be attached to positively charged slides and/or slides coated with poly-L-lysine.

Before a paraffin embedded sample is used for FISH, it is desirable to remove the paraffin in a deparaffinization step. Deparaffinization may be performed by several conventional standard methodologies, such as, for example, incubation in xylenes and a gradually descending series of alcohols (See e.g., "Manual of Histological Staining Method of the Armed Forces Institute of Pathology", supra). Alternatively, commercially available deparaffinizing non-organic agents such as Hemo-De® (CMS, Houston, Tex.) may be used. Unfortunately, current methods for deparaffinization make a sample unsuitable as a substrate for sensitive FISH techniques such as, for example, the detection of nascent RNAs.

2. Preparing Cell-Lines and Tissue for Fluorescence In Situ Hybridization (Sample Preparation, Autofluorescence Reduction), One aspect of the invention is directed to a method for preparing a sample (referred to herein as a tissue sample) for fluorescence in situ hybridization of difficult to detect cellular RNAs such as mRNAs, pre-mRNAs, hnRNAs and nascent RNAs. Preparation is useful to reduce the amount of autofluorescence in a tissue. Thus, in this disclosure, "sample preparation" can also be referred to as "autofluorescence reduction." Preparation may begin immediately after a tissue is fixed as described in section 1 above. Alternatively, the preparation of tissue samples may occur after 1, 2, 4, 5, 10, 15, 20, 25 or 30 years from the time a sample tissue is fixed. As shown in the Examples, the methods of the invention have been successfully performed on aged samples showing that the age of a sample has minimal or no impact on the results.

The method involves the steps of: (a) pressure cooking the sample; and (b) treating the pressure cooked sample with ammonia-ethanol and sodium borohydride.

In a preferred embodiment, the pressure cooking is performed in a decloaking (pressure cooking) chamber at a temperature of about 125° C. reaching a pressure of between about 20 to about 24 PSI (pounds per square inch) for about 30 minutes. These conditions may be reproduced with standard laboratory equipment. Furthermore, specialized decloaking chambers are available from commercial sources such as Biocare Medical (Concord, Calif., USA, catalog number DC2002). During pressure cooking, the sample is contacted with a decloaking solution with deparaffinization and/or antigen retrieval activities. Examples of such solutions include, for example, "Declere™" solution from Cell Marque (Hot Springs, Ariz., USA) or "Reveal™" solution from Bio-Care Medical (Concord, Calif., USA). For example, contact may comprise layering the decloaking solution over a slide containing a tissue section. Alternatively, a slide containing the tissue section may be placed into a solution of decloaking solution and pressure cooked.

In a preferred embodiment, ammonia-ethanol treatment may involve contact with 0.25% ammonia ethanol and sodium borohydrate treatment may involve contact with 5% sodium borohydrate. In a preferred embodiment, ammonia ethanol treatment may be for a period of 20 minutes at room temperature and sodium borohydrate treatment may be for a period of 50 minutes at room temperature. While not essential, reagent contamination may be reduced and reagent life may be extended if the sample is washed in PBS between the decloaking step, the ammonia ethanol treatment step, and the sodium borohydrate step.

As will be apparent to one of skill in the art, this method is ideally suited to fixed-treated cell lines and tissue, particularly paraffin embedded tissue. In a preferred embodiment, the tissue is mammalian. In another preferred embodiment, the mammalian tissue is human.

Accordingly, the present invention is directed towards a pressure cooked composition comprising: (a) a fixed-treated tissue; (b) ammonia-ethanol; and (c) sodium borohydride.

In a preferred embodiment, the ammonia-ethanol concentration is between about 0.1% to about 0.5% (e.g., about 0.25%) in the pressure cooked composition. In another preferred embodiment, the sodium borohydride concentration is about 1% to about 5% (e.g., about 0.5%) in the pressure cooked composition.

In one aspect of the invention, the pressure cooked composition, which has reduced autofluorescence compared to an untreated (not pressure cooked) sample can be used in FISH. Accordingly, in one aspect FISH further comprises a quantification step wherein an mRNA expression level is calculated as a proportion of fluorochrome signal intensity of the mRNA.

In one aspect of the invention, the pressure cooked and treated composition will display reduced autofluorescence as compared to compositions which are not so treated. In one aspect, the composition will display 5%, 10%, 20%, 30%, 40%, 50%, 60%, 70% or more of a reduction in autofluorescence.

The sample preparation methods of the invention may be used for any FISH technique to reduced autofluorescence. As a significant advantage, the pretreatment/sample preparation/antigen reveal method just described does not involve the use of protease or protease stop solutions. In fact, the methods of the invention, mentioned anywhere in this disclosure, does not involve the use of any enzymes or enzymatic reactions.

In an optional step, the sample may be initially probed with a DNA probe to detect the location of chromosomes within the tissue sample. If the tissue sample had intact nuclei, the chromosomes are expected to be located within the nuclei of the tissue sample. Chromosomes in the nuclei can be detected using commercially available chromosomal detection kits (Vysis, Des Plaines, Ill. USA). Briefly, chromosome probes specific for a chromosome may be hybridized to the treated tissue according to manufacturer's instructions. In an optional step, the chromosome locations can then be visualized under fluorescence in the same manner as described for FISH below. Alternatively, the chromosome location may be visualized (detected) after the application of FISH as described in section 3—that is, the chromosome probes may be detected at the same time as the FISH probes of section 3.

Following the hybridization of the chromosome probe/probes, the tissue sample may be washed and immediately used for FISH as described in section 3 below. That is, the chromosomal probe does not have to be removed (stripped) from the sample before the application of the methods described in section 3.

3. Fluorescence In Situ Hybridization "FISH"

In situ hybridization may be performed by several conventional methodologies (See for e.g. Leitch et al. In Situ Hybridization: a practical guide, Oxford BIOS Scientific Publishers, Micropscopy handbooks v. 27 (1994)). In one in situ procedure, fluorescent dyes (such as fluorescein isothiocyanate (FITC) which fluoresces green when excited by a suitable wavelength of light such as that from an Argon ion laser) are used to label a nucleic acid sequence probe which is complementary to a target nucleotide sequence in the cell. Each cell containing the target nucleotide sequence will bind the labeled probe producing a fluorescent signal upon exposure of the cells to the appropriate wavelength.

Various degrees of hybridization stringency can be employed to hybridize a probe or a plurality of probes to nucleic acids in the tissue sample. As the hybridization conditions become more stringent, a greater degree of complementarity is required between the probe and target to form and maintain a stable duplex. Stringency is increased by raising temperature, lowering salt concentration, raising formamide concentration or a combination of these conditions. Adding dextran sulfate or raising its concentration may also increase the effective concentration of labeled probe to increase the rate of hybridization and ultimate signal intensity. After hybridization, slides are washed in a solution generally containing reagents similar to those found in the hybridization solution with washing time varying from minutes to hours depending on required stringency. Longer or more stringent washes typically lower nonspecific background but run the risk of decreasing overall sensitivity.

Probes used in the FISH analysis may be either RNA or DNA oligonucleotides or polynucleotides and may contain not only naturally occurring nucleotides but their analogs like digoxygenin dCTP, biotin dcTP 7-azaguanosine, azidothymidine, inosine, or uridine. Other useful probes include peptide probes and analogues thereof, branched gene DNA, peptidometics, peptide nucleic acid (PNA) and/or antibodies.

Probes should have sufficient complementarity to the target nucleic acid sequence of interest so that stable and specific binding occurs between the target nucleic acid sequence and the probe. The degree of homology required for stable hybridization varies with the stringency of the hybridization medium and/or wash medium. Preferably, completely homologous probes are employed in the present invention, but persons of skill in the art will readily appreciate that probes exhibiting lesser but sufficient homology can be used in the present invention (see for e.g. Sambrook, J., Fritsch, E. F., Maniatis, T., Molecular Cloning A Laboratory Manual, Cold Spring Harbor Press, (1989)). "Complementary," when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency. Naturally, if more than one probe is used, one of skill in the art would know to use probes that do not hybridize to each other (e.g., probe A hybridizing to probe B) or to itself (e.g., forming a hairpin structure).

As used herein, stringency of hybridization may be determined as follows or using other protocols known to one of skill in the art:

1) high stringency: 0.1.times.SSPE, 0.1% SDS, 65° C.
2) medium stringency: 0.2.times.SSPE, 0.1% SDS, 50° C.
3) low stringency: 1.0.times.SSPE, 0.1% SDS, 50° C.

It is understood that equivalent stringencies may be achieved using alternative buffers, salts and temperatures.

One of skill in the art will appreciate that the choice of probe will depend on, for example, the genetic expression or abnormality of interest. Genetic abnormalities that can be detected by this method include, but are not limited to, amplification, translocation, deletion, addition and the like. Probes may also be generated and chosen by several means including, but not limited to, mapping by in situ hybridization, somatic cell hybrid panels, or spot blots of sorted chromosomes; chromosomal linkage analysis; or cloned and isolated from sorted chromosome libraries from human cell lines or somatic cell hybrids with human chromosomes, radiation somatic cell hybrids, microdissection of a chromosome region, or from yeast artificial chromosomes (YACs) identified by PCR primers specific for a unique chromosome locus or other suitable means like an adjacent YAC clone. Probes may be, for example, genomic DNA, cDNA, or RNA cloned in a plasmid, phage, cosmid, YAC, Bacterial Artificial Chromosomes (BACs), viral vector, or any other suitable vector. Probes may be cloned or synthesized chemically by conventional methods.

Probes are preferably labeled with a fluorophore. Examples of fluorophores include, but are not limited to, rare earth chelates (europium chelates), Texas Red, rhodamine, fluorescein, dansyl, phycocrytherin, phycocyanin, spectrum orange, spectrum green, and/or derivatives of any one or more of the above. Multiple probes used in the assay may be labeled with more than one distinguishable fluorescent or pigment color. These color differences provide a means to identify, for example, the hybridization positions of specific probes. Moreover, probes that are not separated spatially can be identified by a different color light or pigment resulting from mixing two other colors (e.g., light red+green=yellow) pigment (e.g., blue+yellow=green) or by using a filter set that passes only one color at a time.

Probes can be labeled directly or indirectly with the fluorophore, utilizing conventional methodology. Additional probes and colors may be added to refine and extend this general procedure to include more genetic abnormalities or serve as internal controls.

4. Analysis of Fluorescence and Technical Applications

After processing for FISH, analysis may be performed by standard techniques of fluorescence (see for e.g. Ploem and Tanke Introduction to Fluorescence Microscopy, New York, Oxford University Press (1987)).

In order to correlate cellular morphology with FISH, one may use a computer-driven, motorized microscope stage on which stores location of coordinates. This may be used to evaluate the same area by two different analytical techniques. For example, color images of the morphologically stained areas may be captured and saved using a computer-assisted cooled CCD camera. The same section (optionally destained) may be subsequently taken through the sample preparation and FISH procedure of the invention and analyzed under fluorescent light one or more times to detect the presences of one or more types of fluorescent molecules. These resulting images may also be stored. Then the images may be superimposed on each other using a computer to determine a correlation of presence of RNAs (including mRNA and nascent RNA), DNAs (chromosomes) and morphology (stained slide). The location of the fluorescence probes can be stored and recalled and designated areas (e.g., prostate ducts) may be scored for the presence of fluorescent nuclear signals. If sequential sections are used, the morphology of the cells and the locations of nucleic acids may be determined in a 3 dimensional reconstruction.

Typically, hundreds of cells are scanned in a tissue sample and quantification of the specific target nucleic acid sequence is determined in the form of fluorescent spots, which are counted relative to the number of cells. Deviation of the number of spots in a test cell from a norm may be indicative of a malignancy or a predisposition to a malignancy, disease, or other abnormality. The relative number of abnormal cells to the total cell sample population may also indicative of the extent of the condition or abnormality. In addition, using family health histories and/or genetic screening, it is possible to estimate the probability that a particular subject has for developing certain types of disease. Those subjects that have been identified as being predisposed to, for example, developing a particular form of disease can be monitored or screened to detect early evidence of disease. Upon discovery of such evidence, early treatment can be undertaken to combat the disease. Similarly, those subjects who have already developed, for example, a malignancy and who have been treated to remove the cancer or are otherwise in remission are particularly susceptible to relapse and reoccurrence, including the metastasis of tumors. Such subjects can be monitored and screened using the presently disclosed methods to detect evidence of metastasis and upon discovery of such evidence, immediate treatment can be undertaken to combat the disease.

Thus, in infected whole blood smears, cell lines or tissue sections, endogenous nucleic acids or nucleic acids of pathogenic organisms such as bacteria, virus, protozoan, or fungi, can be detected within the infected cells. Such methods provide useful diagnostic and scientific information since the presence or absence of a specific nucleic acid can directly or indirectly correlate with one or more cells of observable structure and morphology, and, in this way, provide a basis for clinical diagnosis and prognosis.

For example, scientists, physicians and other investigators attempt to develop compounds or other agents that will have effects on specific molecular pathways in cells that will have a therapeutic effect on disease. The therapeutic action of many of these compounds is expected to result in (directly or indirectly) either suppressing the expression of a gene(s) or, alternatively, the promotion of the expression of that gene(s). In turn, the targeted gene(s), through its suppression or promotion, can either suppress or promote the expression of other genes in molecular pathways that influence the course of disease. Therefore, in order to assess the effect(s) of a putative therapeutic compound or identify toxic effects of a test compound, it would useful to determine if that compound does indeed have the effect of suppressing or promoting genes that are in molecular pathways believed to be involved in the pathogenesis of disease or, in the case of a potential toxic compound, it would be useful to determine if that compound is involved in pathways related to toxic responses.

5. Detecting Pre-mRNA

The earliest expression of a gene is pre-mRNA (including nascent RNA and hnRNA) with the secondary expression resulting in the processing of that pre-mRNA to create mRNA. Therefore, it would be useful to measure pre-mRNA and/or mRNA related to the genes of interest in disease pathogenesis. Such measurements could indicate if a putative compound may indeed work and provide investigators with evidence of whether to proceed with the discovery and development process regarding a specific compound or terminate that process.

Methods for detecting a target nucleic acid fragment directly from a specimen are comprised of multiple steps which are typically performed in the following order. A specimen, usually obtained from a patient, is fixed and embedded in paraffin. The embedded tissue may be sectioned for Tissue-FISH. The sample is treated in keeping with the inventive method (i.e. the sample is pressure cooked and treated with ammonia-ethanol and sodium borohydride). The nucleic acids of the sample are then incubated with a labeled probe specific for the target nucleic acid fragment, under conditions appropriate for hybridization. The probe is comprised of a nucleic acid sequence which is complementary to the target nucleic acid on the tissue under stringent conditions. The probe is then visualized and quantified if necessary. This information can then be compared to a baseline or to another cell or any other desired application as would be apparent to one of skill in the art.

The quantity of the total probe used is a predetermined amount which should exceed the estimated amount of the available target believed to be within the sample (about 100:1) in order to drive the hybridization reaction efficiently and to promote a high rate of probe:target annealing. The labeled probe is incubated with the nucleic acids of the fixed sample. In one embodiment, the labeled probe is generally added in solution onto the sample. Conditions appropriate for hybridization are solutions which provide the appropriate buffered environment. The specific concentration of hybridization buffer varies with the nucleic acid sequence and length of the probe. The exact concentration of buffer used is dependent on the Tm (melting temperature) of the probe, probe sequence, probe length, and hybridization temperature, and can be determined by one of skill in the art through the course of no more than routine experimentation.

After hybridization is complete, the non-hybridized probe is typically rinsed from the sample, generally by applying a series of stringent washes with a wash buffer. It is within the means of those skilled in the art to determine appropriate wash buffers. In one embodiment, the wash buffer is 0.3 M sodium chloride, 0.03 M sodium citrate, and 0.5% NP40. In another embodiment, the wash buffer is phosphate buffered saline (PBS). In a further embodiment, the wash is formamide/sodium citrate.

After rinsing, the sample may be counterstained to allow the visualization of organisms within the cells, which contain the hybridized probes. This staining step is generally applied when a fluorescent-labeled probe is used to detect nucleic acids, which are specific for a pathogen. Counterstaining the cells or tissue concurrently with the in situ hybridization assay enhances the method by allowing a clearer determination of the location of the target nucleic acid within the sample. Such information helps, for example, to provide a clearer determination of background hybridization. In one embodiment, the counterstain is DAPI, Toto-3, To-pro-3, Sytox Green, Yoyo-1, Propidium Iodide, Bobo-3 or Evans Blue.

In one embodiment, any labeled probe that is hybridized to the nucleic acid of the fixed sample is then visually detected by microscopy. The presence of labeled probe within the sample is an indication of the presence of the target nucleic acid fragment. The sensitivity of this method has been determined to detect as little as 10 copies of target nucleic acid.

It should be appreciated that the use of formamide or GuSCN in the hybridization fluid allows hybridization to be carried out at a much lower temperature than standard hybridization protocols. Hybridization of an average probe specifically to the target (and not to host cells) in aqueous hybridization fluid such as sodium chloride would generally require a temperature of 60-65° C. The same hybridization performed at 42° C. in hybridization buffer described above, would provide specificity.

The probe is detected by means suitable for the specific moiety used to label the probe. In one embodiment, the marker moiety is a fluorophore. In a preferred embodiment, the fluorophore is FITC, Fluo-3, 5 hexadecanoyl fluorescein, Cy2, fluorX, Cy3, Cy3.5, Cy5, Cy5.5, Cy7, fluorescein and Texas Red. For example, the preferred method for detecting a fluorescent-labeled probe, employs special filters such as a blue filter (fluorescent labeled probe) and a green filter (for rhodamine-X or Texas red labeled probe).

The methods of this invention may be used for simultaneous detection of different transcripts in a single clinical sample by performing one reaction with a labeled probe, which is comprised of a plurality of different nucleic acid sequences, each labeled with a different marker moiety. For simultaneous detection, the probes that are specific for the different nucleic acids commonly present in a clinical specimen can be designed such that the Tm values of all the probe sequences are very similar. Each specific probe is then labeled with a different detectable moiety (e.g. different fluorescent moieties). Hybridization is performed with the multiple components of the probe. The hybridized sample is processed as described above and the sample is observed by means appropriate for detection of the different labeled probes (e.g. viewed using appropriate filters if different fluorescent moieties are used) to detect which transcripts are detected in the sample.

It will be recognized by practitioners ordinarily skilled in this art that the novel in situ hybridization protocol described herein is compatible with all previously known methods of detection as well as the one described herein. It is expected that the reagents described in the present invention may be provided in a kit form to practice the protocol, which has been optimized for simplicity and for compatibility with a wide variety of detection methods. It is also expected that such prepared kits containing specifically prepared reagents and probes, will be applicable in clinical/diagnostic laboratories, where the ability to detect the presence or absence of specific nucleic acids would serve to positively or negatively identify pathological states characterized by the presence of specific genes. In a preferred embodiment, such methods would be designed for use with fixed treated tissue and would comprise reagents necessary therefore.

Accordingly, in one embodiment, the invention provides a method for identifying a potential therapeutic agent which modulates a level of a gene's expression in a tissue, the method comprising:

(a) preparing at least a first and second sample from at least a first and second tissue according to the inventive process described herein, wherein the samples are identical with the exception that the first tissue has been sampled from a cell-line, animal or human that has been treated with the agent whereas the second tissue has been sampled from a cell-line, animal, or human that has not;

(b) detecting the level of the gene's transcription in the at least first and second tissue using FISH, wherein a difference in the detected levels indicates that the agent modulates the level of the gene's expression. In one preferred embodiment, the modulation of the gene's expression is comprised in a pathway associated with therapeutic effects on the cell-line, animal, or human. Identification of a favorable response to a particular agent may be critical in assessing potential therapeutic effects of candidate therapeutic agents. In another preferred embodiment, the modulation of the gene's expression is comprised in a pathway associated with toxic effects on the cell line, animal, or human. Identification of a toxic response to a particular agent may be critical in assessing potential detrimental effects of candidate therapeutic agents.

6. Detection of Nascent RNA

The invention is based in part on the development of a robust multiplex fluorescent in situ hybridization "FISH" technique in archival formalin-fixed, paraffin-embedded (FFPE) human tissue sections which allows the preservation of the microanatomical context. The method identifies single cell gene expression patterns by probing multiple, unique nascent RNA transcripts and yields predictive quantitative gene expression signatures. The method allows detection of signal foci from multiple nascent RNA localized at the transcription site of expressing genes. The presence of nascent RNA directly correlates with early events of gene regulation in response to external or physiologic stimuli (Wilson A J, et al. Cancer Res. 62, 6006-6010 (2002)). This provides an opportunity to quantitatively evaluate the temporal expression pattern of multiple genes in single nuclei.

Integrating histological features and molecular profiles enhances our understanding of cellular response to microenvironment and elucidates biological mechanisms of disease processes. This will allow the improvement of patient management by assisting in early diagnosis and objective patient prognosis including outcome and response to treatment. As an example, gene expression signatures in prostate tumor and normal cells from patients were investigated.

Most gene expression analyses, unlike FISH studies, extract RNA from solubilized tissue, which destroys cellular architecture such that expression profiles can not be associated with specific cell types. Analysis of small samples excludes the detection of a large number of potentially interesting low abundance gene products. Lack of standardization and reproducibility and amplification bias limit the interpretation of expression data resulting from methods such as RNA amplification and quantitative PCR (Lockhart, D. J. and E. A. Winzeler Nature 405(6788): 827-36 (2000); Enders G. Acta Neurochir Suppl. 89, 9-13 (2004); Hoffmann K, Firth M J, Freitas J R, de Klerk N H, Kees U R Mol Biotechnol. 29, 31-38 (2005).

According one aspect of the invention relates to an adapted, robust fluorescent in situ hybridization "FISH" technique (Bubendorf L., et al. J Pathol 195, 72 (2001); Capodieci P., et al. Diagn Mol Pathol 7, 69 (1998)) for identifying multiple, unique nascent RNA transcripts in single nuclei from paraffin embedded tissue sections (peT-FISH). This method will provide the basis by which to interrogate multiple genes in archival material and to correlate this data with clinicopathological variables and patient outcome.

A key feature to the technology is the detection of nascent RNA transcripts using a spectral "bar code" that allows multiplexing of many genes simultaneously within a single cell (Levsky, J. M., et al. Science 297, 836 (2002)). Optionally, the method utilizes automated fluorescence microscopy and analysis to detect nascent RNA in archival tissue specimens from both whole section or Tissue Microarray (TMA) format, allowing for high-throughput gene expression analysis and prognosis. Accessing the transcription sites in routine processed tissue sections, or on stained slides, is achieved by improving antigen retrieval methods (Capodieci P., et al. J Natl Cancer Inst. 96, (2004)) in a novel way to reveal molecular targets for nucleic acid hybridization.

Robust expression information was detected of five genes from formalin-fixed, paraffin embedded (FFPE) samples of which the majority are 10-15 years old and one sample was 22 years old, without diminution in the nascent RNA signal when compared to more recent specimens (FIG. 1A). Chromosome-specific probes were used to verify the location and identity of the expressed nascent transcript sites, as in this case for the androgen receptor (AR) gene (FIG. 1B). It was therefore possible to optimize the use of archival patient sample collections, including the added capability of performing peT-FISH analyses on 'de-stained' hematoxylin and eosin (H&E) tissue sections. This last feature is especially important when a patient's tissue blocks are exhausted or no longer available. In the example shown, a paraffin section was re-stained with H&E after peT-FISH and images taken for superimposition of the morphologic data with the gene expression results (FIG. 1, C-E). Transcription sites were detected and analyzed using a computer software program that identified the site and decoded the identity of each gene based on the spectral barcode. The cumulative data were then exported to a spreadsheet for correlation with morphological features in the stained sample. The next step was to investigate how multiplex in situ gene expression profiling would correlate with histopathologic features. The classification of transcription sites was restricted to the epithelial cells associated with benign prostate tissue, prostatic intraepithelial neoplasia (PIN), prostate cancer (PCa) and prostate cancer metastasis (PCaMet) (Glinsky G., et al., J Clin Invest. 113, 913 (2004)). The procedure was modified for a high-throughput sampling of patient material by enabling the assessment of multiple patient samples in a tissue microarray (TMA) format (Capodieci P., et al. J Natl Cancer Inst. 96, (2004)). The evaluation of 59 patients from a PCa progression TMA indicated that the expression patterns allowed identification and subsetting of tumor-specific cells in all patient samples evaluated (FIGS. 1F-H). The transcription pattern for AR, PSMA, AMACR and JAG1 was more prominent in PCa samples when compared with benign prostate tissue, focal PIN and PCaMet. Importantly, the five genes yielded statistically significant, disease-specific combinatorial differences (FIG. 1F, red). Discrete classes of patient samples were manifested by unique gene expression "fingerprints" for unique histopathological types, suggesting true biological similarities. In contrast to the epithelium, there was no signal identified in the nuclei of the non-cancerous stromal fibroblasts or endothelial cells in the cases evaluated. These results indicate that the peT-FISH technology will be useful in facilitating the development of an integrated molecular and cellular roadmap of clinical disease.

By evaluating gene activity within various signaling pathways and gene response networks the methods of the invention have the capability to elucidate the morphological features of disease and to decode mechanisms of pathogenesis. A reasonable comparison to peT FISH is with the recent methods available to extract and analyze RNA from FFPE tissues using RT-PCR or cDNA expression microarrays (Cronin M et al., Amer J Pathol 164, 35 (2004); Paik et al., NEJM 351, 2817 (2004); Lewis F., et al., J Pathol. 195, 66 (2001)). With these applications the major requirement and thus limitation is the necessity to destroy the cytoarchitecture of the primary sample. An important secondary aspect is that the integrity of the transcription site is retained irrespective of the degradation of the RNA, which is occurring in FFPE tissue over time (data not shown). Therefore peT FISH, is the only technology that allows true in situ multiplex gene expression while retaining the morphology of the tissue specimen. This is particularly relevant since the published association between gene expression profiles and changes in cellular morphology in human tissue samples is extremely rare. Only recently was the transcriptional co-activator p300 (previously linked to prostate cancer progression, Debes et al., Cancer Res 63, 7638 (2002)) and the nuclear lamins shown to modulate nuclear morphology in prostate cancer epithelial cells (Debes et al., Cancer Res 65, 708 (2005)). Suitable nascent RNA targets for the diagnosis of prostate cancer include for example, GalNAc-T3 (UDP-N-Acetyl-α-D-galactosamine transferase), PSMA, Hepsin and DD3/PCA3 (Prostate cancer antigen 3). Suitable nascent RNA targets for evaluating the prognosis (i.e., clinical failure/progression) of prostate cancer include for example, Wnt5a (wingless-type MMTV integration site family member 5), KFL6 (Kruppel-like factor 6), EI24/SSR1, EPB 4.9, Map4K4 AR, and ER alpha (PCA3/DD3). Suitable nascent RNA targets for the determination of poor outcome/aggressive phenotype (i.e. androgen independent) for prostate cancer include for example, BCL2, BCLx1, Clusterin, Hsp27 and AR.

The data with peT FISH supports a link between pathologic correlates and gene expression profiles which has the potential to modify present day tumor grading systems, achieved only with on-slide based analyses. The ultimate goal will be to utilize these key signatures to establish predictive and prognostic markers based on their association with clinical outcome data.

EXAMPLES

Example 1

Material and Methods

Samples

Microarrays (TMA) consisting of 0.6 mm core biopsies of formalin-fixed, paraffin-embedded tissues were created using a tissue arrayer (Beecher Instrument). Cohorts of 59 anonymized prostate samples present in the TMA in triplicate were analyzed. Of the 59 patients, 20 were prostate adenocarcinoma (PCa), 12 were benign prostatic hyperplasia (BPH), 13 were prostatic intraepithelial neoplasia (PIN), 14 were prostate metastasis (PCaMet).

Sample Preparation—Pretreatment

5 μm paraffin-embedded sections were dried at 37° C. for about 1 hour and then transferred to a decloaker chamber for 30 minutes where they were deparaffinized and antigen-retrieved using a solution that allows both steps to occur at the same time. The slides were then washed in PBS for 10 minutes, incubated for 20 minutes in 0.25% ammonia-ethanol at room temperature (RT), and then incubated for 50 minutes in 5% sodium borohydride in PBS at RT. The slides were then washed twice with tap water and then in PBS for 5 minutes.

Hybridization

The slides were incubated for at least 15 minutes in a prehybridization solution of formamide/2×SSC at RT. The slides were then hybridized with a specific set of probes at 37° C. in a humidity chamber from 3 hours to overnight. The slides then underwent several post-hybridization washes which included:

Formamide/2×SSC for 20 minutes at 37° C.
1×SSC at RT on a shaker for 15 minutes
0.5×SSC at RT on a shaker for 15 minutes The slides were then washed in PBS/MgCl$_2$ for 5 minutes and then the nuclei were counterstained using a DAPI solution (Blue). The slides were rinsed in PBS/MgCl$_2$ for 5 minutes to remove the excess solution, and then mounted and placed under a coverslip using an antifade mounting solution. The slides were kept at −20° C. until the actual reading under the fluorescent microscope.

Oligonucleotide Probe Synthesis

Four 50-mer DNA probes were synthesized for each target transcript. Sequences were designed with OLIGO-6.0 (Molecular Biology Insights) and verified for specificity using the BLAST program at NCBI GeneBank. Amine-modified Thymidine bases were used as substrates for amidation using commercially available succinimidyl ester conjugates of fluorescent dyes. For experiments shown here the fluorophores used to label these oligonucleotides were Cy3, Cy3.5, Cy5 and Cy5.5 (Amersham).

The oligonucleotide sequences are as follows:

```
AMACR probe 1:
                                            (SEQ ID NO: 1)
gtgcttagagggagatcatgaacaccaagacaaaaggcctggatgcaacc AMACR probe 2:
                                            (SEQ ID NO:2)
ggcttgtaacttaactcagtccaaggagacacaaaacgacttgctggggg AMACR probe 3:
                                            (SEQ ID NO:3)
gatgaagaaacctgctccaccttcctcttgcgattgttgaacggcagttg AMACR probe 4:
                                            (SEQ ID NO:4)
ttccttccaccatatttgcatcaatgacctgacccttgccagtgcgtgtg AR probe 1:
                                            (SEQ ID NO:5)
cttccacatgtgagagctccatagtgacacccagaagcttcatctccaca AR probe 2:
                                            (SEQ ID NO:6)
tctccttcctcctgtagtttcagattaccaagtttcttcagcttccgggc AR probe 3:
                                            (SEQ ID NO:7)
catagccttcaatgtgtgacactgtcagcttctgggttgtctcctcagtg AR probe 4
                                            (SEQ ID NO:8)
tgtgcatgcggtactcattgaaaaccagatcaggggcgaagtagagcatc JAG1 probe 1:
                                            (SEQ ID NO:9)
ccacctcccggctttctttccttctctcgcgctcccctttcttttattatt JAG1 probe 2:
                                            (SEQ ID NO:10)
acacggctgatgagtcccacagtaattgagatctttgtcacagagctggc JAG1 probe 3:
                                            (SEQ ID NO:11)
agcgataaccattaaccaaatcccgacaggaggcgtcattctgacactgg JAG1 probe 4:
                                            (SEQ ID NO:12)
agtagtagtcatcacaggtcacgcggatctgatactcaaagtgggcaacg PSMA probe 1:
                                            (SEQ ID NO:13)
ggtaaagtctctctcaatctcactaatgcctcgcttatcagccctgcagg PSMA probe 2:
                                            (SEQ ID NO:14)
aggattttaaaaccacccgaagaggaagccgaggagaaagaagccaccc PSMA probe 3:
                                            (SEQ ID NO:15)
gggtaggacaacaggacatcataatgtgctagctcaacagaatcaggcc PSMA probe 4:
                                            (SEQ ID NO:16)
aggtccaacattgtagggcactttgagacttcctctccagctgctatctg EPB49 probe 1:
                                            (SEQ ID NO:17)
gccggctggtgcagacagtaagtgaattatgaaacgaggcaagtcatcca EPB49 probe 2:
                                            (SEQ ID NO:18)
gcagagagcgggttttccttcggatcggcaatgacttttccatctcttct EPB49 probe 3:
                                            (SEQ ID NO:19)
ggggccccaataaattacattcttgagagagcatagtgtgtgaggggggtg EPB49 probe 4:
                                            (SEQ ID NO:20)
tatagatgggaggcttcttgtagatgttggaatctgggcgggaggtctca
```

Barcoding

Each of the four dyes was viewed using the appropriate filter set (Chroma) using an Olympus BX51 with a UPlanApo 1.4 60× objective and a Roper CoolSnap camera. Each set of labeled probes was mixed to achieve the appropriate barcode: EBP4.9: Cy3 & Cy5; JAG-1: Cy3.5 & Cy5; PSMA: Cy3.5 & Cy3; AMCAR: Cy3.5 & Cy5.5; AR: Cy3, Cy3.5, Cy5. For the Chromosome FISH: Chromosome Cy3 & AR Cy3.5 & Cy5.

Experimental Design

The inability to detect a given transcription site is a reflection of a number of components including on/off gene function, low signal to noise ratio and the qualities of the tissue section including anatomic location and section thickness. In order to address this issue, multiple probes were experimentally employed for a single housekeeping gene/transcription site, with the intention of increasing the signal to noise ratio as well as determining the overall sensitivity and specificity of the assay. The housekeeping genes SMG-1, a phospatidylinositol 3-kinase-related protein kinase and beta-actin were selected. The number of SMG-1 transcription sites detected by peT-FISH was unchanged when the number of oligonucleotide probes targeting SMG-1 ranged from 8 to 82 (FIGS. 1a, 1b); however, six probes detected 50% fewer transcription sites (data not shown). This indicated the optimal number of probes required to detect transcription reproducibly and robustly. Simultaneous peT-FISH and DNA FISH confirmed the specificity of transcription site detection, as signal from nascent RNA and the gene were coincident (FIG. 1c). Signal from DNA FISH targeting a different gene did not correlate with peT-FISH signal (data not shown). Detection of nascent transcripts was not restricted to freshly prepared tissue samples. This method robustly detected expression of five genes from archived FFPE tissue samples of which the majority were collected and fixed 10 to 15 years before peT-FISH with one sample collected and fixed 22 years before peT-FISH (FIG. 1d).

A series of 41, 16, 8, 4 and 3 unique 50 mer oligonucleotides were generated across the entire gene and individually labeled with Cy3 and Cy5, in order to generate 82, 32, 16, 8, and 6 independent probes, respectively. These analyses were performed on FFPE Tissue Microarray sections from a series of normal tissues as well as benign and cancerous prostate tissues.

It was determined that the number and integrity of the transcription sites was constant from 82 to 8 probes with a diminution of signal identified when only six probes were utilized in the assay. Subsequent peT FISH studies were therefore performed with 8 labeled oligonucleotide probes.

Tissue-FISH

Briefly, Tissue Microarray sections were baked in a dry oven at 65° C. for 30 minutes and subsequently placed in a de-cloaking buffer used as deparaffinization and antigen retrieval agent for about 30 minutes. After 5 minutes of cooling at room temperature followed by three washes in tap water and two in PBS, the sections were further processed through successive treatments in order to reduce auto-fluorescence: ammonia-alcohol (0.25%) for 20 min. followed by sodium borohydride (5%) for 40 min. Autofluorescence at all wavelengths was observed to be reduced by more than half. Pre-hybridization was performed at room-temperature in 50% formamide/2×SSC for a minimum of 15 minutes followed by hybridization with 20 ng of probe for 2 hours at 37° C. in a humidified chamber in the dark. Post-hybridization washes were conducted at room temperature on a shaker in the dark as follow: 50% formamide/2×SSC for 20 minutes, 2×SSC, 1×SSC and 0.5×SSC for 15 minutes each. After a brief wash with PBS the slides are counterstained with DAPI and mounted with Antifade (Vysis). 20×SSC comprise 175.3 g NaCl and 88.2 g Sodium Citrate per liter.

Image Acquisition and Analysis.

Three-dimensional image data were acquired using an BX61 microscope (Olympus) with a CoolSNAP HQ Charge-Coupled Device (CCD) camera (Photometrics) using IPLab Software Windows version 3.7 (Scanalytics). We used UPlanApo 20×, 40× 1.0 NA and 60× 1.4 NA objectives (Olympus) and HiQ Band pass filters for DAPI, FITC, Cy3, Cy3.5, Cy5, Cy5.5 (SP filter set, Chroma Technology).

Slides were evaluated at 20× magnification to review overall section quality and at 40× and 60× for the distribution of the fluorescence signal (nascent transcript spots). To be scored as a true transcription site, our experimental criteria required simultaneously detection of at least two colors at a site, independent hybridization events highly unlikely to be attributable to chance. Only sites on nuclei are counted. The number of nuclei in each field examined is also counted, including those in fields where transcription sites are not detected, to determine the relative frequency of occurrence of these sites.

Transcription sites were detected with software that analyzed the image data collected in three dimensions, from six independent fluorescence channels. The data collected from the Cy3, Cy3.5, Cy5 and Cy5.5 fluorescence channels corresponded to the dyes used to label the FISH probes. The data collected in the FITC channel were representative of autofluorescence in the specimen, as no FISH probe was labeled with a dye that fluoresced in this channel. The data collected in the DAPI channel provided the boundaries of nuclei in the specimen. The FITC, Cy3, Cy3.5, Cy5 and Cy5.5 image data were convolved using a classic 4×4 spatial high pass filter and then segmented using a threshold with morphological constraints on object volume and shape. The objective of these steps was to reject fluorescing artifacts and high intensity voxel noise. The segmented data from each of these fluorescent channels were then binarized. The DAPI image data were thresholded, interior holes in segments were filled and the data were binarized, which provided a three dimensional binary map of nuclear positions. The binarized data from the Cy3, Cy3.5, Cy5 and Cy5.5 channels were masked using the binarized nuclear data multiplied by the inverted binarized FITC data. This yielded binarized image data in Cy3, Cy3.5 and Cy5 that represented nuclear FISH signal that was not coincident with autofluorescence. Using simple binary operators to interpret the FISH barcode scheme, the Cy3, Cy3.5, Cy5 and Cy5.5 resultant image data were combined into a single image volume in which each binarized object was encoded with a gene identity. The centroid of each encoded object was reported in a tabular text file and marked and numbered with a pseudo color and number assigned to each gene on a blue pseudo colored, two-dimensional maximum projection of the acquired DAPI image data.

Example 2

Patient Analysis by Microarray

To investigate how peT-FISH data correlate with histopathologic features, epithelial cells with established pathologic morphologies: benign prostate tissue, prostatic intraepithelial neoplasia (PIN), prostate cancer (PCa) and prostate cancer metastasis (PCaMet, Glinsky G., et al. J Clin. Invest. 113, 913-923 (2004)) was examined. peT-FISH was performed on 'de-stained' hematoxylin and eosin (H&E) tissue sections (FIG. 3). The ability to use destained section is an important capability because in many cases, patient tissue blocks are no longer available for analysis. The panels show overlays of peT-FISH results on morphology image data. The procedure was modified for high-throughput sampling of patient material in TMA format (Capodieci P., et al. J Natl Cancer Inst. 96, (2004)).

Random fields were chosen from each individual from tissue microarray (TMA) blocks representing tissue samples derived from patients that had undergone therapeutic and/or diagnostic procedures for PCa at two facilities. The individual patient samples were selected from several TMAs and represent PCa progression series exhibiting a full range of clinical and pathologic patient features.

Mean Number of Transcription Sites (with Standard Error of the Mean) per 100 Cells for each Diagnosis

| Tissue | AMACR | PSMA | AR | EPB4.9 | JAG-1 | Samples |
| --- | --- | --- | --- | --- | --- | --- |
| PCa | 9.3 (1.5) | 10.5 (1.5) | 12.9 (1.4) | 3.2 (0.5) | 3.8 (0.3) | 20 |
| PIN | 5.0 (0.7) | 4.8 (0.6) | 8.3 (1.5) | 4.0 (0.7) | 3.1 (0.4) | 13 |
| PCaMet | 4.1 (1.0) | 3.7 (0.8) | 5.4 (0.7) | 0.9 (0.2) | — | 14 |
| Benign | 2.3 (0.3) | 3.9 (0.4) | 4.5 (0.5) | 3.0 (0.4) | 2.5 (0.3) | 12 |

Example 3

Analysis of Tissue Sections

We have determined that the resolution provided by current microscopes is sufficient for detecting the expression of up to 40,000 transcription sites in a cell simultaneously. Our reasoning is as follows. The nucleus is approximately 10 μm in diameter which corresponds to a volume of approximately 500 μm$^3$ (V=$\frac{4}{3}(\pi r^2)$). A voxel is approximate 0.1 μm by 0.1 μm by 0.25 μm or 2.5×10$^{-3}$ μm$^3$. Thus, there are 200,000 voxels per nucleus which corresponds to a detection ability of about 40,000 transcription sites. Approximately 10,000 genes are expected to be transcribed in a nucleus simultaneous. Thus, the microscopic technique of the invention is capable of detecting all the expressed genes in a cell at the same time.

Our experimental strategy is based on detection of nascent RNA. Nascent RNAs are RNAs that are being transcribed from genomic DNA (i.e., chromosome). Since the RNAs are still being transcribed, they are associated with their corresponding gene and chromosome by multiple proteins including, for example, RNA polymerase and the like. Since the RNA is still attached to the chromosome, the colocalization of an RNA probe and a chromosome probe will allow an operator to determine both the expression level of a nascent RNA and the chromosomal location of the gene which encodes the nascent RNA. Since most cells are diploid, nascent RNA would be expected to be transcribed in two locations in a nucleus if both chromosomes of a diploid genome are transcriptionally active. Furthermore, since chromosomal regions may be amplified in aneuploidy cells (chromosomal duplication, uneven translocation, microsatellite chromosomes), 3, 4, 5 or more transcription sites in a nucleus are not unexpected.

Figure 4:
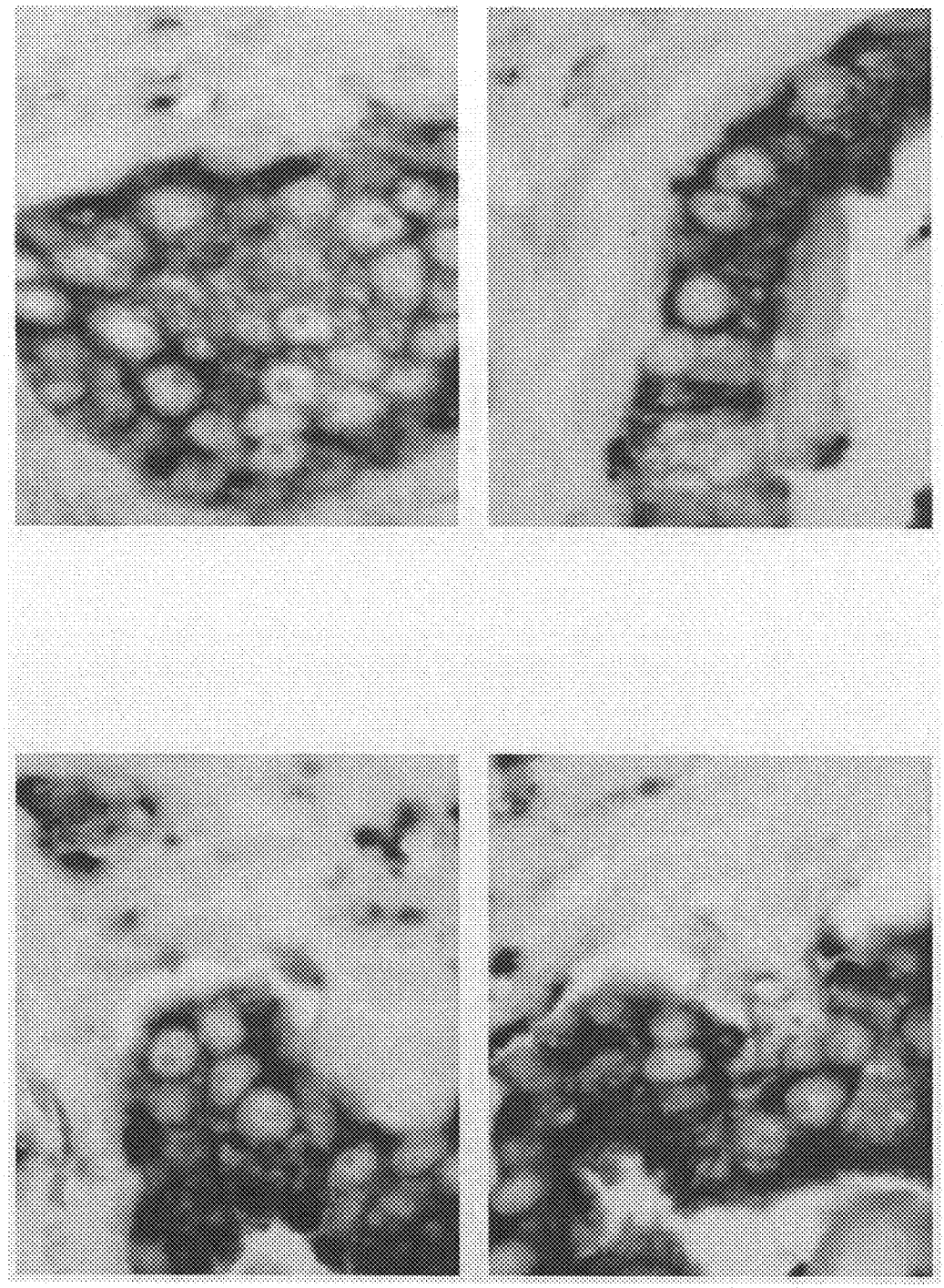
FIG. 4 depicts the detection of rRNA from fresh frozen prostate cancer sections using non-isotopic in situ hybridization (NISH). The results show that RNA is present and has not been degraded in the tissue sample.
Figure 5:
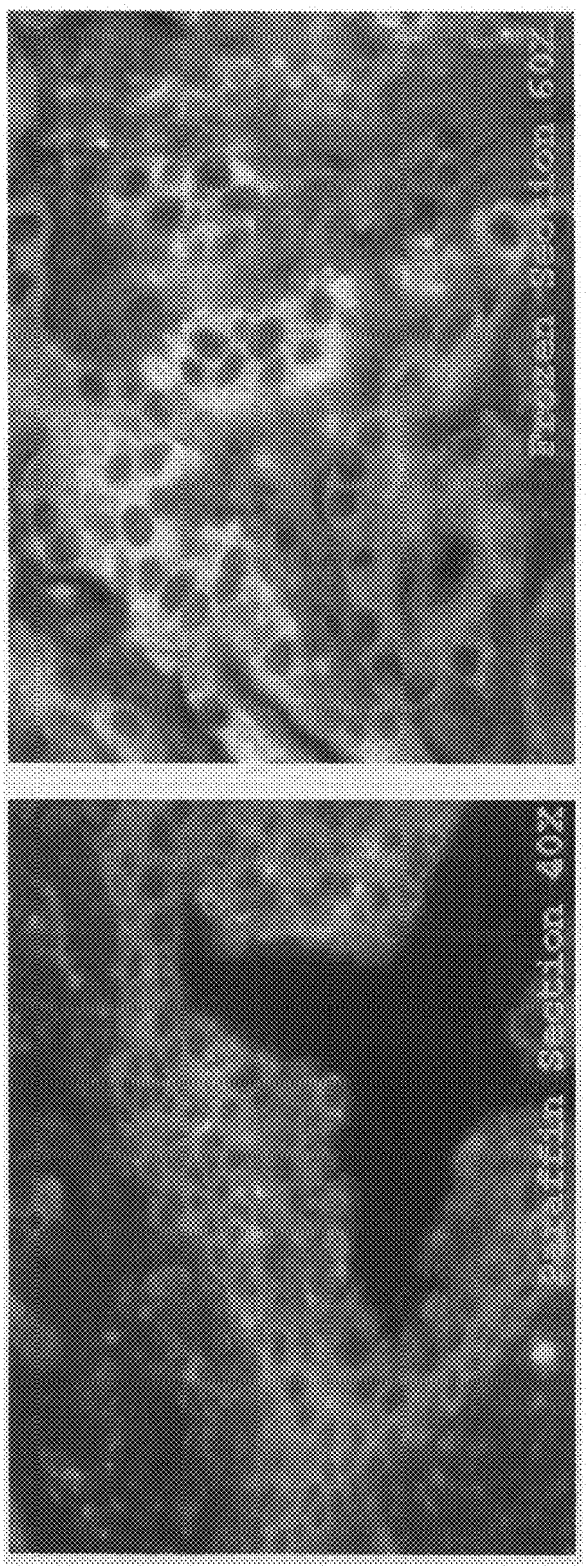
FIG. 5 depicts the detection for the expression of rRNA from formalin-fixed, paraffin-embedded (FFPE) prostate cancer sections (left panel) or frozen section (right panel) using non-isotopic fluorescent in situ hybridization. The results show diffused expression of cytoplasmic rRNA within tumor epithelial cells.

To show that cellular and nucleus RNA are not degraded by the sample preparation method of the invention, we probed fresh frozen prostate cancer sections with a probe specific for ribosomal RNA. As seen in FIGS. 4 and 5, ribosomal RNA is detectable in the cytoplasm and in the nuclei of the cells in the section. The ribosomal RNA in the nucleus represents nascent ribosomal RNA and ribosomal RNA that have not been transported to the cytoplasm. FIG. 4 shows a H&E stained section while FIG. 5 shows a similar tissue section viewed under fluorescence.

Figure 6:
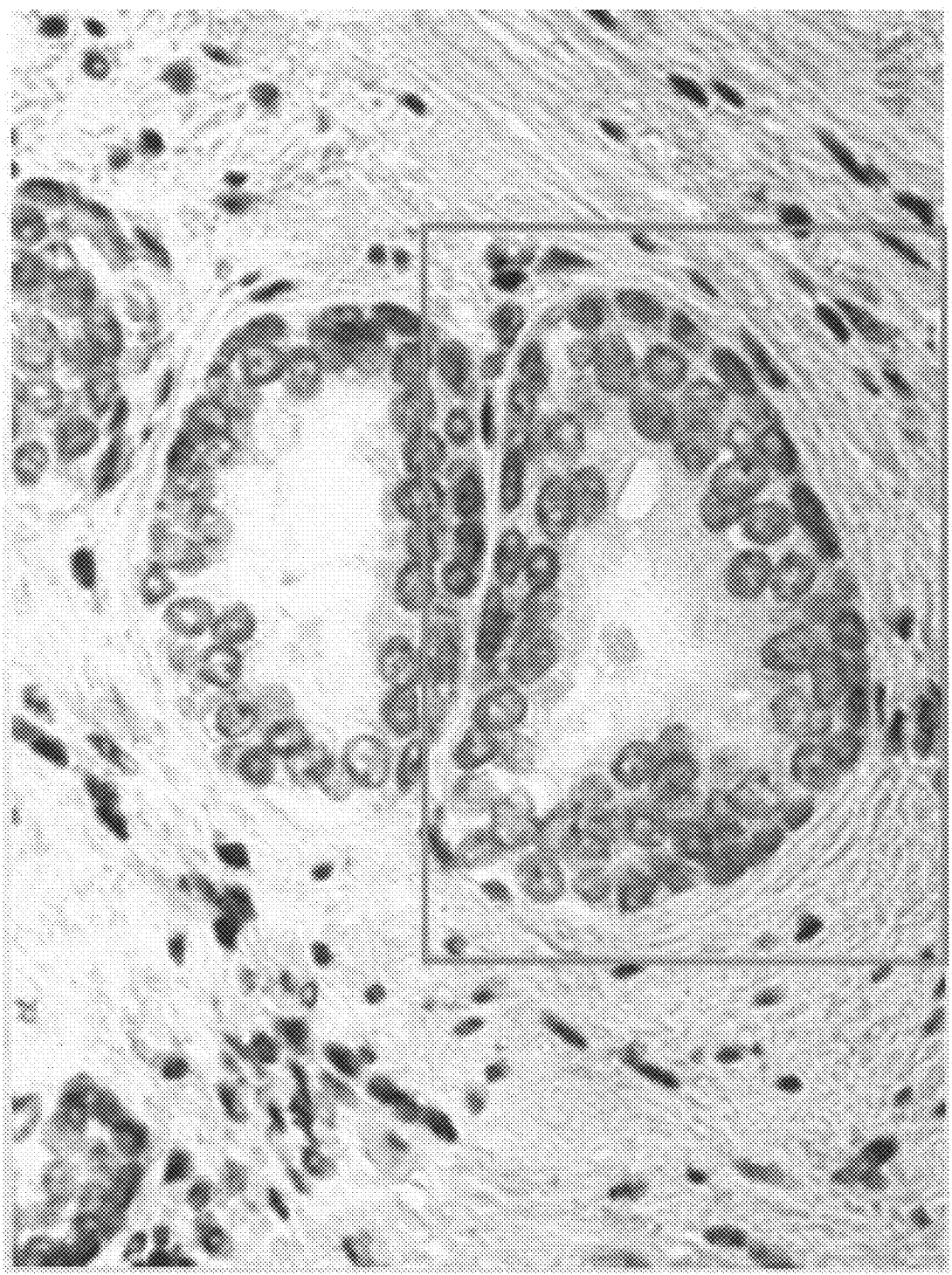
FIG. 6 depicts a hematoxylin and eosin stained section of a prostate gland exhibiting some features of prostatic intraepithelial neoplasia (PIN).

To further show feasibility, the sample preparation and pet-FISH methods of the invention were applied to a previously H&E stained prostate gland section (FIG. 6). The same section was probed using a total of 8 probes specific for AR. Four of the probes were labeled with Cy3 (encoded in red in FIG. 7) and 4 of the probes were labeled with Cy3.5 (encoded in green in FIG. 7). FIG. 7 is a computer enhanced FISH image clearly shows the colocalization of the Cy3 and Cy3.5 signals indicating the presence of the AR gene. It should be noted that the color assigned to the dyes are coded by computer and does not represent the actual color of these fluorescent moieties.

Figure 8:
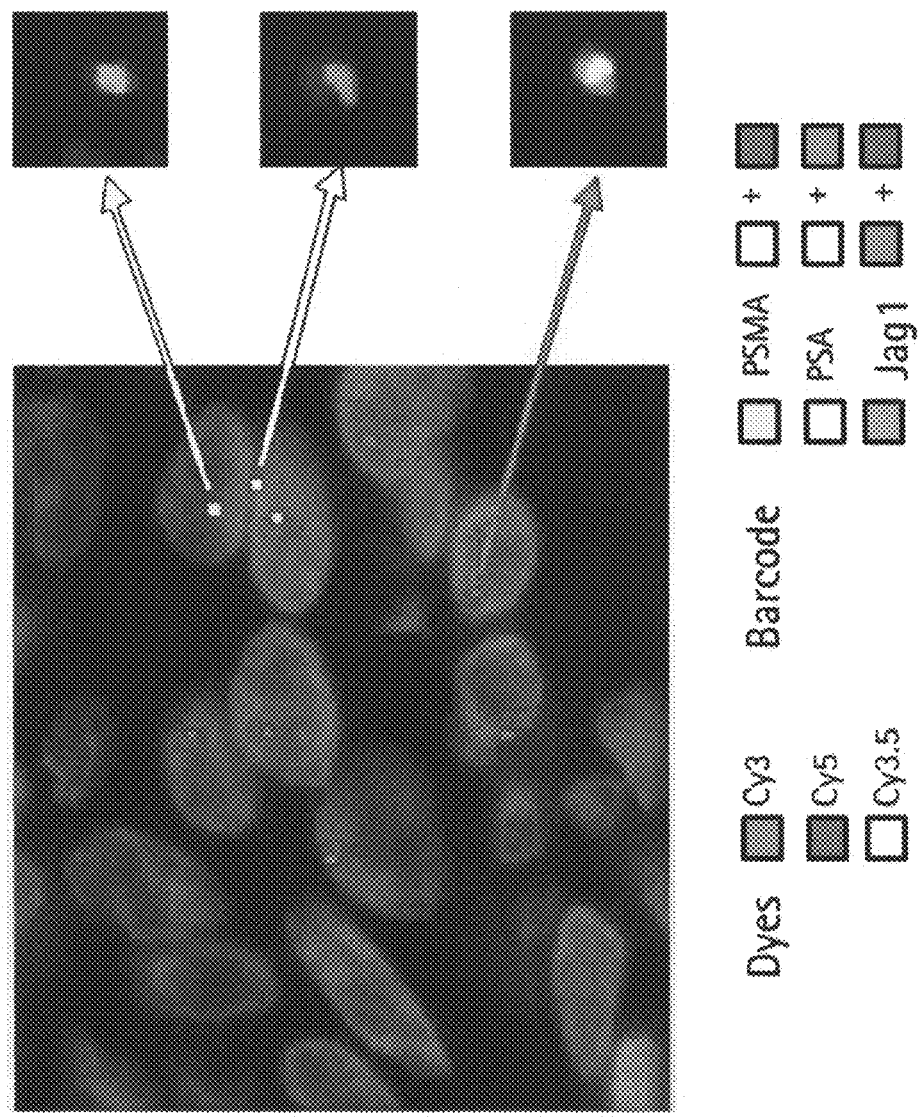
FIG. 8 depicts the results of the Multiplex Spectral Barcoding Method. The picture depicts a prostate tumor section treated with the sample preparation methods of the invention and probed with the pet-FISH method of the invention. In the applied bar coding scheme, Jag1 is detected as a combination of Cy3 (red) and Cy5 (green) fluorescence, PSMA is detected as a combination of Cy3.5 (white) and Cy5 (green) fluorescence, PSA is detected as a combination of Cy3 (red) and Cy3.5 (white) fluorescence. Detection was performed using automated transcription site detection based on machinery and protocols developed at Aureon. Expression of PSMA, PSA and Jag1 are clearly seen.

FIG. 8 shows a different prostate sample which underwent the same experimental procedure as FIG. 7 with the exception that different probes were used. Briefly, 24 probes were used and each probe is a 50 bases long oligonucleotide with a unique nucleic acid sequence. PSMA probes comprise 4 different oligonucleotides labeled with CY3.5 and 4 different oligonucleotides labeled with Cy5. PSA probes comprise 4 different probes labeled with Cy3.5 and 4 different probes labeled with Cy3. Jag1 probes comprise 4 different probes labeled with Cy3 and 4 different probes labeled with Cy5. All 24 probes were used simultaneously and the result is shown in FIG. 8. As can be seen, PSMA, PSA and Jag1 were each localized to different regions of the nucleus and their locations were distinguishable from each other.

To further explore the technology, pet-FISH was performed using 36 probes specific for 4 genes as follows:
Jag1: Cy5 (4 probes)+Cy3 (4 probes)
PSMA: Cy3.5 (4 probes)+Cy5 (4 probes)
PSA: Cy3 (4 probes)+Cy3.5 (4 probes)
AR: Cy3.5 (4 probes)+Cy3 (4 probes)+Cy5 (4 probes)

Figure 9:
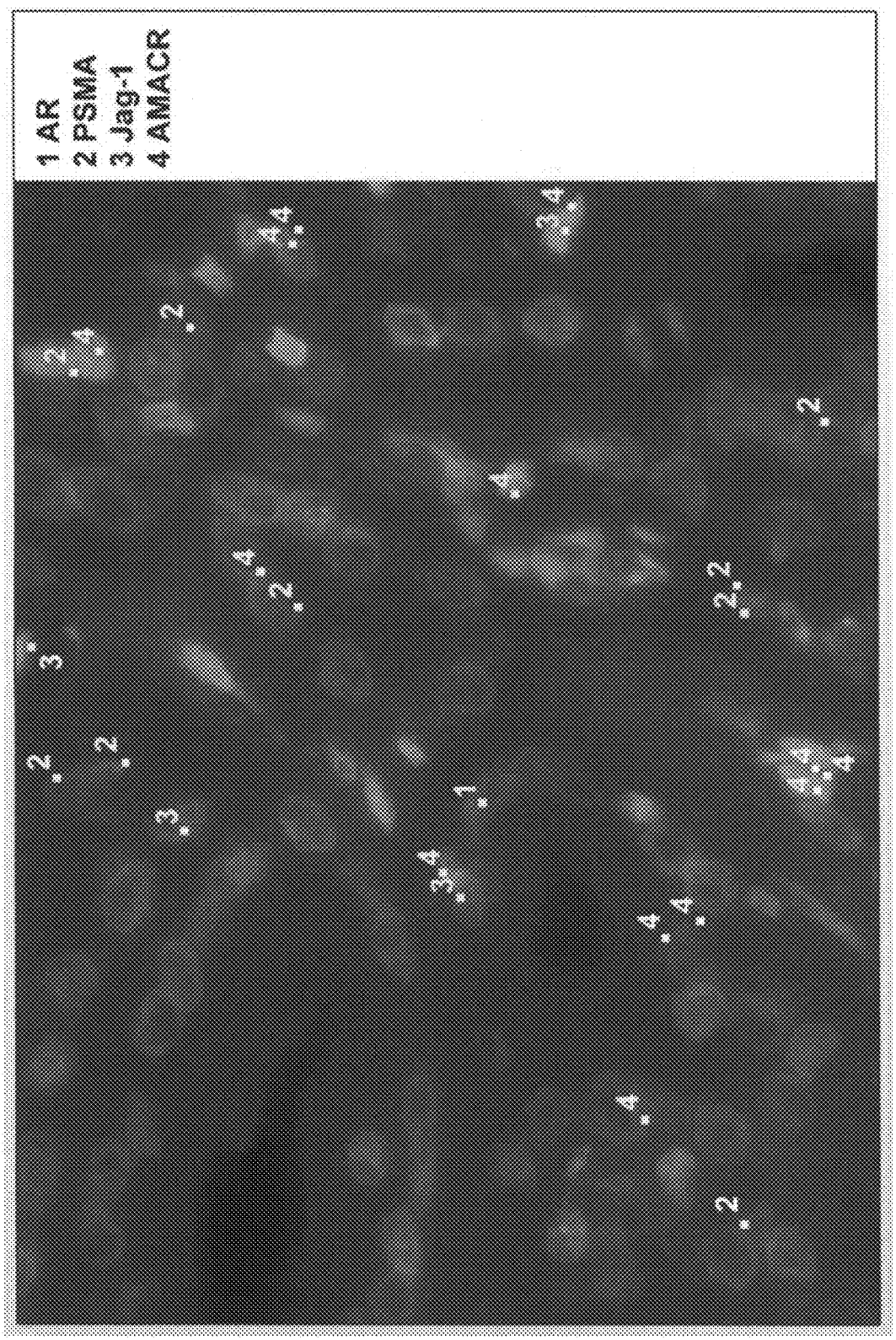
FIG. 9 depicts the use of the Multiplex Spectral Barcoding Method to simultaneous detect 4 genes: Jag-1, PSMA, PSA and AR. In this barcoding scheme, Jag1 is detected as a combination of Cy5 (yellow) and Cy3 (green), PSMA is detected as a combination of Cy3.5 (red) and Cy5 (yellow), PSA is detected as a combination of CY3 (green) and Cy3.5 (red), and AR is detected as a combination of Cy3.5 (red), Cy3 (green) and Cy5 (yellow). In this Figure, a 22 year old sample was used as the starting material.

Sample preparation and pet-FISH were performed as described above. An automated analysis of tissue microarray was performed. The result of the procedure on a tissue microarray is shown in FIG. 9. By using Automated Nascent Transcript Analysis, expression of various genes in the nucleus was located to specific regions of the nucleus as follows:

| # | centroid-x | centroid-y | gene |
|---|------------|------------|------|
| 1 | 215.7 | 304.7 | AR |
| 2 | 258.4 | 724.8 | PSMA |
| 3 | 395.5 | 586 | PSMA |
| 4 | 433 | 612.5 | PSMA |
| 5 | 452 | 253.5 | Jag1 |
| 6 | 520 | 53 | PSMA |
| 7 | 563 | 230.3 | PSMA |
| 8 | 730 | 189.6 | PSMA |
| 9 | 781 | 473 | AMACR |
| 10 | 933.4 | 401.9 | PSMA |
| 11 | 940.5 | 680.5 | PSMA |
| 12 | 977.2 | 461.1 | PSMA |
| 13 | 1057 | 259 | PSMA |
| 14 | 1164 | 588 | Jag1 |
| 15 | 1168.6 | 719.4 | PSMA |

Figure 10:
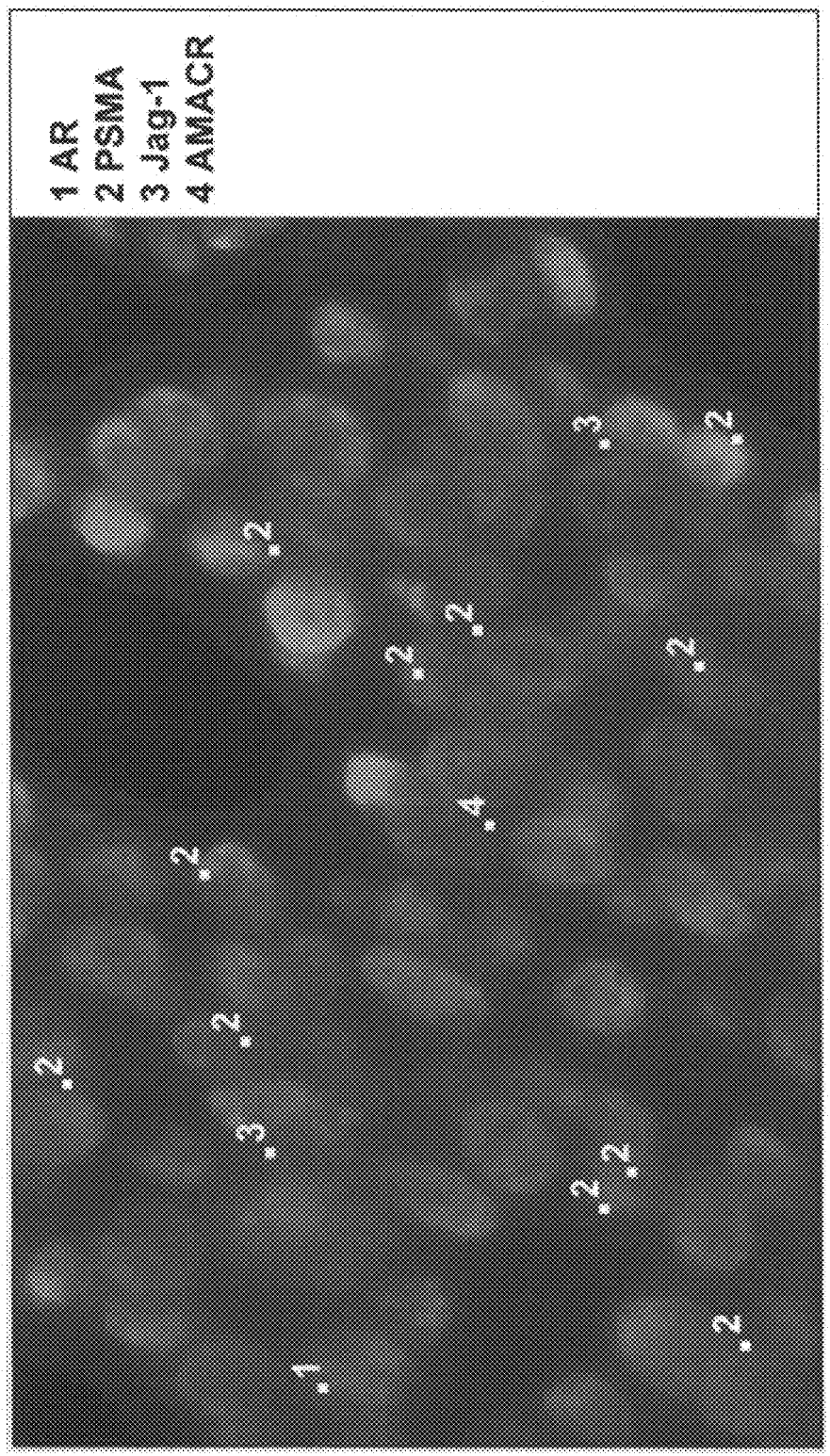
FIG. 10 depicts the results of a second experiment performed using the same method as FIG. 12 except the starting material is from a tissue microarray.

The same experiment was repeated using tissue from a tissue microarray using a 22 year old sample (FIG. 10). As can be seen, there is no significant difference between the quality of the data from the new sample (FIG. 9) and the 22 year old sample (FIG. 10). This shows that the method of the invention is capable of analyzing samples prepared more than 20 years ago.

REFERENCES

1. Bubendorf L., et al. J Pathol 195, 72 (2001); 2. Capodieci P., et al. Diagn Mol Pathol 7, 69 (1998); 3. Femino, A. M., et al. Science 280, 585 (1998); 4. Levsky, J. M., et al. Science 297, 836 (2002; 5. Kosman D., et al. Science, 305, 846 (2004); 6. Capodieci P., et al. J Natl Cancer Inst. 96, (2004); 7. Glinsky G., et al., J Clin Invest. 113, 913 (2004); 8. Shou J., et al. Cancer Res. 61, 19 (2001); 9. Cronin M et al., Amer J Pathol 164, 35 (2004); 10. Paik et al., NEJM 351, 2817 (2004); 11. Lewis F., et al., J Pathol. 195, 66 (2001); 12. Debes et al., Cancer Res 63, 7638 (2002); 13. Debes et al., Cancer Res 65, 708 (2005); 14. hypertexttext-transferprotocol://worldwideweb.nature.com; 15. U.S. Pat. No. 6,995,020 filed Jul. 21, 2003 and issued Feb. 7, 2006; 16. Lockhart, D. J. and E. A. Winzeler Nature 405 (6788): 827-36 (2000); 17. Enders G. Acta Neurochir Suppl. 89, 9-13 (2004); 18. Hoffmann K, Firth M J, Freitas J R, de Klerk N H, Kees U R Mol Biotechnol. 29, 31-38 (2005); 19. Wilson A J, et al. Cancer Res. 62, 6006-6010 (2002); 20. Glinsky G., et al. J Clin Invest. 113, 913-923 (2004); 21. Heighway J et al. Oncogene 21, 7749-7763 (2002); 22. van de Vijver M J et al. NEJM 347, 1999-2009 (2002); 23. Lu et al. Nature, 435, 834-838 (2005); 24. Bussemakers M J et al. Cancer Res. 59, 5975-5979 (1999).

We claim:

1. A method for the in situ detection of one or more nascent RNA species in a human paraffin embedded tissue sample comprising the steps of:
   a) performing autofluorescence reduction on the human paraffin embedded tissue sample by pressure cooking the tissue sample at a temperature of about 125° C., at a pressure of between 20 to 24 PSI and for a period of 10 minutes to 1 hour to produce a pressure cooked sample, and then treating said pressure cooked sample with ammonia-ethanol at a concentration of 0.1% to 0.5% for between 10 and 50 minutes and sodium borohydride at a concentration of 1% to 5% for between 10 and 50 minutes in any order;
   b) hybridizing at least one labeled nucleic acid probe specific for one or more nascent RNA species to the tissue sample;
   c) detecting the at least one labeled nucleic acid probe in the tissue sample thereby detecting the presence of the one or more nascent RNA species.

2. The method of claim 1 wherein the tissue sample is from a neoplastic or preneoplastic tissue.

3. The method of claim 1 wherein the ammonia-ethanol is in a concentration of 0.25%.

4. The method of claim 1 wherein treating the pressure cooked sample with ammonia-ethanol comprises contacting the pressure cooked sample with ammonia-ethanol for 10 to 30 minutes.

5. The method of claim 1 wherein treating the pressure cooked sample with ammonia-ethanol comprises contacting the pressure cooked sample with ammonia-ethanol for 40 minutes.

6. The method of claim 1 wherein treating the sample with sodium borohydride comprises contacting the pressure cooked sample with sodium borohydride for 20 minutes.

7. The method of claim 1 wherein the at least one labeled nucleic acid probe is attached to at least one fluorescent moiety.

8. The method of claim 7 wherein the fluorescent moiety is selected from the group consisting of FITC, Cy3, Cy3.5, Cy5, Cy5.5 and DAPI.

9. The method of claim 7 wherein each of said nascent RNA species hybridizes to a plurality of probes with a unique combination of fluorescent moieties for each of said nascent RNA species.

10. The method of claim 7 wherein each of said nascent RNA species hybridizes to 8 or more probes.

11. The method of claim 7 wherein each of said nascent RNA species hybridizes to 12 or more probes.

12. The method of claim 1 wherein the labeled nucleic acid probe comprises a nucleotide sequence of an intron, a 5' untranslated region or a 3' untranslated region of a nascent RNA.

13. The method of claim 1 wherein the labeled nucleic acid probe is specific for a 5' region of the nascent RNA species.

14. The method of claim 1 wherein the labeled nucleic acid probe is specific for a 3' region of the nascent RNA species.

15. The method of claim 1 further comprising a step of staining the sample after the detecting step.

16. The method of claim 1 wherein the detecting step comprises the step of detecting the labeled nucleic acid probe in the nucleus of a cell in the tissue sample.

17. The method of claim 1 wherein the detecting step detects the labeled nucleic acid probe within 50 micron of its location.

18. The method of claim 1 further comprising the step of determining the location of a chromosome in said tissue sample.

19. The method of claim 1 which is performed in the absence of any added protease.

20. The method of claim 18 wherein determining the location of a chromosome comprises the steps of
   (1) hybridizing at least one labeled chromosome specific probe to said tissue sample;
   (2) detecting said at least one labeled chromosome specific probe in at least one cell in said tissue sample.

21. The method of claim 20 wherein the step of detecting the labeled chromosome specific probe detects the labeled chromosome specific probe within 50 micron of its location.

22. The method of claim 18 wherein said step of determining the location of a chromosome is performed after step a), after step b), or after step c).

* * * * *